United States Patent [19]

Baker et al.

[11] Patent Number: 5,760,018

[45] Date of Patent: Jun. 2, 1998

[54] GEM-DISUBSTITUTED AZACYCLIC TACHYKININ ANTAGONISTS

[75] Inventors: Raymond Baker, Much Hadham; Richard Thomas Lewis, Harlow; Angus Murray MacLeod, Bishops Stortford; Graeme Irvine Stevenson, Saffron Walden, all of United Kingdom

[73] Assignee: Merck Sharp & Dohme Ltd., Hoddesdon, England

[21] Appl. No.: 676,152

[22] PCT Filed: Jan. 12, 1995

[86] PCT No.: PCT/GB95/00057

§ 371 Date: Jul. 11, 1996

§ 102(e) Date: Jul. 11, 1996

[87] PCT Pub. No.: WO95/19344

PCT Pub. Date: Jul. 20, 1995

[30] Foreign Application Priority Data

Jan. 13, 1994 [GB] United Kingdom .................. 9400542
Feb. 17, 1994 [GB] United Kingdom .................. 9403072

[51] Int. Cl.$^6$ .............. A61K 31/445; C07D 211/22; C07D 211/26
[52] U.S. Cl. ............... 514/63; 514/317; 514/318; 514/314; 514/322; 514/326; 514/331; 546/14; 546/176; 546/178; 546/191; 546/199; 546/209; 546/210; 546/212; 546/214; 546/229; 546/236
[58] Field of Search ................... 546/14, 176, 178, 546/194, 199, 209, 210, 212, 214, 229, 236; 514/63, 317, 318, 314, 322, 326, 331

[56] References Cited

U.S. PATENT DOCUMENTS 5,620,989 4/1997 Harrison et al. .................. 514/317
5,661,162 8/1997 Macleod et al. .................. 514/331

FOREIGN PATENT DOCUMENTS

| 0 285 032 | 10/1988 | European Pat. Off. . |
| 0 474 561 | 3/1992 | European Pat. Off. . |
| WO 93 21181 | 10/1993 | WIPO . |
| WO 94 10165 | 5/1994 | WIPO . |
| WO 94 13639 | 6/1994 | WIPO . |
| WO 94 19323 | 9/1994 | WIPO . |

*Primary Examiner*—Richard L. Raymond
*Attorney, Agent, or Firm*—J. Eric Thies; David L. Rose

[57] ABSTRACT

The present invention is directed to certain compounds represented by structural formula I:

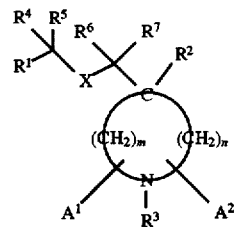

or a pharmaceutically acceptable salt thereof wherein $R^1$, $R^2$, $R^3$, $R^4$, $R^5$, $R^6$, $R^7$, $A^1$, $A^2$, X, m and n are defined herein. The compounds of this invention are tachykinin receptor antagonists and are of particular use in the treatment of pain, inflammation, migraine and emesis.

11 Claims, No Drawings

GEM-DISUBSTITUTED AZACYCLIC TACHYKININ ANTAGONISTS

This application is a 371 of PCT/GB95/00057, filed Jan. 12, 1995.

This invention relates to a class of azacyclic compounds, which are useful as tachykinin antagonists. More particularly, the compounds of the invention comprise an azacyclic ring system substituted by an arylmethyloxy or arylmethylthio moiety.

The tachykinins are a group of naturally occurring peptides found widely distributed throughout mammalian tissues, both within the central nervous system and in peripheral nervous and circulatory systems.

At present, there are three known mammalian tachykinins referred to as substance P, neurokinin A (NKA, substance K, neuromedin L) and neurokinin B (NKB, neuromedin K) (for review see J. E. Maggio, *Peptides* (1985) 6(suppl. 3), 237–242). The current nomenclature designates the three tachykinin receptors mediating the biological actions of substance P, NKA and NKB as the $NK_1$, $NK_2$ and $NK_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, *J. Auton. Pharmacol.* (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 *Substance P in the Nervous System*, Ciba Foundation Symposium 91, 13–34 (published by Pitman) and Otsuka and Yanagisawa, "Does Substance P Act as a Pain Transmitter?" *TIPS* (1987) 8, 506–510], specifically in the transmission of pain in migraine (B. E. B. Sandberg et al, *J. Med Chem*, (1982) 25, 1009) and in arthritis [Levine et al *Science* (1984) 226, 547–549]. Tachykinins have also been implicated in gastrointestinal (GI) disorders and diseases of the GI tract such as inflammatory bowel disease [Mantyh et al *Neuroscience* (1988) 25(3), 817–37 and D. Regoli in *"Trends in Cluster Headache"* Ed. Sicuteri et al Elsevier Scientific Publishers, Amsterdam (1987) page 85)] and emesis [F. D. Tattersall et al, *Eur. J. Pharmacol.*, (1993) 250, R5–R6]. It is also hypothesised that there is a neurogenic mechanism for arthritis in which substance P may play a role [Kidd et al "A Neurogenic Mechanism for Symmetrical Arthritis" in *The Lancet*, 11 November 1989 and Grönblad et al, "Neuropeptides in Synovium of Patients with Rheumatoid Arthritis and Osteoarthritis" in *J. Rheumatol.* (1988) 15(12), 1807–10]. Therefore, substance P is believed to be involved in the inflammatory response in diseases such as rheumatoid arthritis and osteoarthritis, and fibrositis [O'Byrne et al, *Arthritis and Rheumatism* (1990) 33, 1023–8]. Other disease areas where tachykinin antagonists are believed to be useful are allergic conditions [Hamelet et al, *Can. J. Pharmacol.*

*Physiol.* (1988)66, 1361–7], immunoregulation [Lotz et al, *Science* (1988) 241, 1218–21 and Kimball et al, *J. Immunol.* (1988) 141(10), 3564–9] vasodilation, bronchospasm, reflex or neuronal control of the viscera [Mantyh et al, *PNAS* (1988) 85, 3235–9] and, possibly by arresting or slowing β-amyloid-mediated neurodegenerative changes [Yankner et al, *Science* (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, *Cancer Research* (1992) 52, 4554–7].

Substance P may also play a role in demyelinating diseases such as multiple sclerosis and amyotrophic lateral sclerosis [J. Luber-Narod et al, poster C.I.N.P. XVIIIth Congress, 28th June-2nd July 1992], and in disorders of bladder function such as bladder detrusor hyper-reflexia (Lancet, 16th May 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

In view of their metabolic instability, peptide derivatives are likely to be of limited utility as therapeutic agents. It is for this reason that non-peptide tachykinin antagonists are sought.

In essence, this invention provides a class of potent non-peptide tachykinin antagonists.

The present invention provides a compound of the formula (I) or a pharmaceutically acceptable salt thereof:

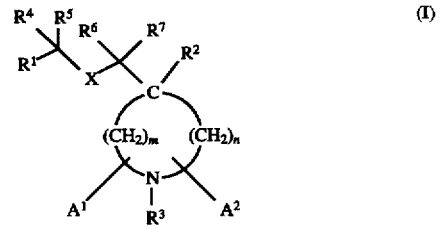

wherein $A^1$ and $A^2$ each independently represent hydrogen or $C_{1-4}$alkyl;

m is 2, 3 or 4;

n is zero, 1 or 2 when m is 2 or 3 and n is zero or 1 when m is 4;

$R^1$ represents phenyl optionally substituted by 1, 2 or 3 groups selected from $C_{1-6}$alkyl, $C_{2-6}$alkenyl, $C_{2-6}$alkynyl, $C_{3-6}$cycloalkyl, $C_{3-6}$cycloalkyl$C_{1-4}$alkyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$COR^a$, —$CO_2R^a$ or —$CONR^aR^b$, where $R^a$ and $R^b$ each independently represent H, $C_{1-6}$alkyl, phenyl or trifluoromethyl;

$R^2$ represents phenyl optionally substituted by 1, 2 or 3 groups selected from $C_{1-6}$alkyl, $C_{2-6}$alkenyl, $C_{2-6}$alkynyl, $C_{3-6}$cycloalkyl, $C_{3-6}$cycloalkyl$C_{1-4}$alkyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$CO_2R^a$ or —$CONR^aR^b$, where $R^a$ and $R^b$ are as previously defined; heteroaryl selected from indazolyl, thienyl, furyl, pyridyl, thiazolyl, tetrazolyl and quinolyl; benzhydryl; or benzyl; wherein each heteroaryl and each phenyl moiety of benzyl and benzhydryl may be substituted by $C_{1-6}$alkyl, $C_{3-6}$cycloalkyl, $C_{3-6}$cycloalkyl$C_{1-4}$alkyl, $C_{1-6}$alkoxy, halo or trifluoromethyl;

$R^3$ represents H, $COR^9$, $CO_2R^{10}$, $COCONR^{10}R^{11}$, $COCO_2R^{10}$, $SO_2R^{15}$, $CONR^{10}SO_2R^{15}$, $C_{1-6}$ alkyl optionally substituted by a group selected from ($CO_2R^{10}$, $CONR^{10}R^{11}$, hydroxy, cyano, $COR^9$, $NR^{10}R^{11}$, $C(NOH)NR^{10}R^{11}$, $CONHphenyl(C_{1-4}alkyl)$, $COCO_2R^{10}$, $COCONR^{10}R^{11}$, $SO_2R^{15}$, $CONR^{10}SO_2R^{15}$ and phenyl optionally substituted by 1, 2 or 3 substituents selected from $C_{1-6}$alkyl, $C_{3-6}$cycloalkyl, $C_{3-6}$cycloalkyl$C_{1-4}$ alkyl, $C_{1-6}$alkoxy, halo and trifluoromethyl), Y—$R^8$ or CO—Z—$(CH_2)_q$—$R^{12}$;

$R^4$ represents $C_{1-6}$-alkyl substituted by a hydroxy group, or $(CH_2)_pNR^{10}R^{11}$, $CO_2R^{16}$, $CONR^{10}R^{11}$, $(CH_2)_pCO_2R^{16}$, $(CH_2)_pCONR^{10}R^{11}$, $(CH_2)_pNR^{10}COR^{18}$, $(CH_2)_p NR^{10}SO_2R^{15}$, $(CH_2)_pOR^{16}$, $(CH_2)_pOC(O)R^{10}$ or $(CH_2)_pO(CH_2)_rCOR^{17}$;

$R^5$ represents hydrogen or $C_{1-6}$alkyl optionally substituted by a hydroxy group, or $(CH_2)_pNR^{10}R^{11}$, $CO_2R^{16}$, $CONR^{10}R^{11}$, $(CH_2)_pCO_2R^{16}$, $(CH_2)_pCONR^{10}R^{11}$, $(CH_2)_pNR_{10}COR^{18}$, $(CH_2)_pNR^{10}SO_2R^{15}$, $(CH_2)_pOR^{16}$, $(CH_2)_pOC(O)R^{10}$ or $(CH_2)_pO(CH_2)_rCOR^{17}$;

or $R^4$ and $R^5$ together with the carbon atom to which they are attached form a $C_{3-6}$cycloalkyl ring which may be substituted by 1 or 2 groups selected from $C_{1-6}$alkyl, $C_{1-6}$alkoxy, hydroxy or $C_{1-6}$alkyl substituted by hydroxy;

$R^6$ and $R^7$ each independently represent H or $C_{1-6}$alkyl;

$R^8$ represents an optionally substituted aromatic heterocycle;

$R^9$ represents H, $C_{1-6}$alkyl, $C_{3-6}$cycloalkyl, $C_{3-6}$cycloalkyl$C_{1-4}$alkyl, or phenyl;

$R^{10}$ and $R^{11}$ each independently represent H or $C_{1-6}$alkyl;

$R^{12}$ represents $NR^{13}R^{14}$ or an optionally substituted aromatic or non-aromatic azacyclic or azabicyclic group;

$R^{13}$ and $R^{14}$ each independently represent H, $C_{1-6}$alkyl, phenyl optionally substituted by 1, 2 or 3 groups selected from $C_{1-6}$alkyl, $C_{1-6}$-alkoxy, halo or trifluoromethyl, or phenyl$C_{1-4}$alkyl optionally substituted in the phenyl ring by 1, 2 or 3 groups selected from $C_{1-6}$alkyl, $C_{1-6}$alkoxy, halo or trifluoromethyl;

$R^{15}$ represents $C_{1-6}$alkyl, trifluoromethyl or phenyl optionally substituted by 1, 2 or 3 substituents selected from $C_{1-6}$alkyl, $C_{1-6}$alkoxy, halo and trifluoromethyl;

$R^{16}$ represents $C_{1-6}$alkyl;

$R^{17}$ represents $C_{1-6}$alkoxy, amino, $C_{1-4}$alkylamino or di($C_{1-4}$alkyl)amino;

$R^{18}$ represents $C_{1-6}$alkyl, $NR^{13}R^{14}$ or an optionally substituted aromatic or non-aromatic azacyclic or azabicyclic group;

X represents O or $NR^{19}$ where $R^{19}$ represents hydrogen or $C_{1-6}$alkyl;

Y represents a hydrocarbon chain of 1, 2, 3 or 4 carbon atoms which may optionally be substituted by oxo;

Z represents $CH_2$, O, S or $NR^{10}$;

p represents an integer from 1 to 4;

q represents zero or an integer from 1 to 6; and r represents an integer from 1 to 4.

As used herein, the definition of each expression, when it occurs more than once in any structure, is intended to be independent of its definition elsewhere in the same structure.

The alkyl, alkenyl and alkynyl groups referred to with respect to the formulae herein may represent straight, branched or cyclic groups, or combinations thereof. Thus, for example, suitable alkyl groups include methyl, ethyl, n- or iso-propyl, n-, sec-, iso- or tert-butyl.

The cycloalkyl groups referred to with respect to the above formula may represent, for example, cyclopropyl, cyclobutyl, cyclopentyl or cyclohexyl. Similarly, cycloalkyl-alkyl groups may be, for example, cyclopropylmethyl.

Suitable alkenyl groups include vinyl and allyl; and suitable alkynyl groups include propargyl.

The term "halo" as used herein includes fluoro, chloro, bromo and iodo, especially chloro and fluoro.

Those compounds according to the invention which contain one or more chiral centres may exist both as enantiomers and as diastereomers. It is to be understood that all such isomers and mixtures thereof are encompassed within the scope of the present invention.

$A^1$ and $A^2$ which may be attached to any carbon atom or atoms in the ring, are aptly hydrogen or methyl and are preferably both hydrogen.

Preferably m is 2.

When m is 2, n is preferably 2. When m is 3 or 4, n is preferably zero.

Preferably $R^1$ represents substituted phenyl. When $R^1$ is substituted phenyl suitable substituents include nitro, trifluoromethyl, trimethylsilyl, bromo, chloro, fluoro, iodo, cyano, methyl, ethyl, cyclopropyl, t-butyl, vinyl, methoxy, phenoxy, amino and carbonylmethoxy. Preferably $R^1$ represents phenyl substituted by 1, 2 or 3 groups selected from $C_{1-6}$alkyl such as methyl and t-butyl, halo such as chloro, fluoro and bromo, and trifluoromethyl.

Preferably $R^1$ represents disubstituted phenyl, in particular 3,5-disubstituted phenyl, for example 3,5-disubstituted phenyl wherein the substituents are selected from $C_{1-6}$alkyl, halo and trifluoromethyl. More preferably $R^1$ represents 3,5-bis(trifluoromethyl)phenyl. Also preferred are those compounds wherein $R^1$ represents 3-fluoro-5-(trifluoromethyl)phenyl.

Suitable values for the group $R^2$ include unsubstituted or substituted phenyl, 5-membered heteroaryl such as thienyl, 6-membered heteroaryl such as pyridyl, and benzhydryl.

Preferably $R^2$ represents unsubstituted or substituted phenyl.

When $R^2$ represents substitued phenyl a preferred substituent is halo, especially fluoro.

When $R^4$ represents $C_{1-6}$alkyl substituted by a hydroxy group, this may be, for example, $CH_2OH$, $CH_2CH_2OH$, $CH(OH)CH_3$ or $C(OH)(CH_3)_2$, especially $CH_2OH$.

Preferably $R^4$ is $C_{1-6}$alkyl substituted by hydroxy, or $(CH_2)_pNR^{10}R^{11}$, $(CH_2)_pCONR^9R^{10}$, $CO_2R^{16}$, $(CH_2)_p NR^{10}COR^{18}$, $(CH_2)_pNR^{10}SO_2R^{15}$, $(CH_2)_pOR^{16}$, $(CH_2)_pOC(O)R^{16}$ or $(CH_2)_pO(CH_2)_rCOR^{17}$, or $R^4$ together with $R^5$ and the carbon atom to which they are attached forms a $C_{3-6}$cycloalkyl ring.

When $R^5$ represents $C_{1-6}$alkyl optionally substituted by a hydroxy group, this may be, for example, methyl or hydroxymethyl.

When $R^4$ and $R^5$ together with the carbon atom to which they are attached form a $C_{3-6}$cycloalkyl ring, this may be for example, cyclopropyl, cyclobutyl or cyclopentyl, especially cyclopropyl.

When $R^8$ represents a substituted aromatic heterocycle, suitable substituents in the heterocyclic ring include 1, 2 or 3 groups selected from $C_{1-6}$alkyl, $C_{3-6}$cycloalkyl, $C_{3-6}$cycloalkyl$C_{1-4}$alkyl, $C_{1-6}$alkoxy, phenyl, oxo, thioxo, halo, trifluoromethyl, $NR^aR^b$, $NR^aCOR^b$, $CONR^aR^b$, $CO_2R^a$, $SR^a$, $SO_2R^a$ and $CH_2OR^a$, where $R^a$ and $R^b$ are as previously defined. Particular examples of suitable substituents include methyl, methoxy, phenyl, oxo, thioxo, bromo, iodo, $NH_2$, $SCH_3$, $CONH_2$ and cyano. Particularly preferred substituents include oxo and $NH_2$.

Suitable values for $R^8$ include thienyl, furyl, pyrrolyl, pyridyl, pyrazolyl, triazolyl, tetrazolyl, thiazolyl, pyrazinyl, pyrimidinyl, pyridazinyl, triazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl, any of which may be substituted.

Preferably $R^8$ represents a substituted or unsubstituted 5- or 6-membered nitrogen containing aromatic heterocycle such as for example oxazolyl, oxadiazolyl, tetrazolyl, thiazolyl, thiadiazolyl, triazolyl, pyrazinyl, pyridyl, pyrimidinyl, pyridazinyl, imidazolyl or triazinyl. More preferably $R^8$ represents optionally substituted oxazolyl, oxadiazolyl, imidazolyl, thiadiazolyl, triazolyl, pyrazinyl, pyrimidinyl, pyridazinyl or triazinyl, or tetrazolyl substituted by $C_{1-6}$alkyl, preferably methyl.

Also preferred are those compounds in which $R^8$ represents an optionally substituted triazolyl group, particularly a triazolinone group.

It will be appreciated that, when the heterocyclic moiety $R^8$ is substituted by an oxo or thioxo substituent, different tautomeric forms are possible so that the substituent may be represented as =O or —OH, or =S or —SH, respectively. For the avoidance of doubt, all such tautomeric forms are embraced by the present invention.

When $R^{12}$ represents $NR^{13}R^{14}$, $R^{13}$ and $R^{14}$ are preferably both $C_{1-6}$alkyl such as methyl, ethyl, n-propyl, i-propyl, n-butyl, i-butyl or t-butyl. More preferably $R^{13}$ and $R^{14}$ will both represent methyl.

When $R^{12}$ represents an aromatic or non-aromatic azacycle or azabicycle it may contain 1, 2 or 3 additional heteroatoms selected from O, S and N or groups $NR^{16}$, where $R^{16}$ is H, $C_{1-6}$alkyl or phenyl$C_{1-4}$alkyl, and may be unsubstituted or substituted. Suitable substituents include $C_{1-6}$alkyl, $C_{3-6}$cycloalkyl, $C_{3-6}$cycloalkyl$C_{1-4}$alkyl, $C_{1-6}$alkoxy, oxo, SH, =S, halo, trifluoromethyl, $NR^aR^b$, $NR^aCOR^b$, $CONR^aR^b$, $CO_2R^a$ and $CH_2OR^a$, where $R^a$ and $R^b$ are as previously defined.

When $R^{12}$ represents an aromatic azacycle or azabicycle, suitable values of $R^{12}$ include imidazolyl, triazolyl, tetrazolyl, oxazolyl, thiazolyl, pyrrolyl, pyrazolyl, pyrazinyl, pyridyl, oxadiazolyl, thiadiazolyl, isoxazolyl, isothiazolyl, benzimidazolyl, benzoxazolyl and indolyl, preferably imidazolyl, such as 2,4-imidazolyl, or pyridyl, more preferably pyridyl such as 4-, 3- or 2-pyridyl.

When $R^{12}$ represents a non-aromatic azacycle or azabicycle, suitable values of $R^{12}$ include morpholinyl, piperdinyl, pyrrolidinyl, piperazinyl, methylpiperazinyl, azanorbornanyl, azabicyclo[2.2.2]octanyl and azabicyclo [3.2.2]nonyl, preferably morpholinyl, pyrrolidinyl, methylpiperazinyl, quinuclidinyl (azabicyclo[2.2.2]octanyl) or azabicyclo[3.2.2]nonyl, more preferably pyrrolidinyl.

Suitably Y represents a hydrocarbon chain of 1 or 2 carbon atoms optionally substituted by oxo, such as $CH_2$, C=O, $CH(CH_3)$, $CH_2CO$ or $COCH_2$. Preferably Y represents $CH_2$, $CH(CH_3)$ or $CH_2CO$, more preferably $CH_2$ or $CH(CH_3)$.

Suitably q represents zero, 1, 2 or 3.

Suitable values of $R^3$ include H, $COR^9$ such as $COCH_3$, $SO_2R^{15}$ such as $SO_2CH_3$, $C_{1-6}$alkyl such as $CH_3$, $CH(CH_3)_2$, $CH_2CH(CH_3)_2$ and $CH_2CH_2C(CH_3)_3$, $C_{1-6}$alkyl substituted by $CO_2R^{10}$ such as $CH_2CO_2CH_3$, $CH_2CO_2H$, $(CH_2)_3CO_2CH_3$ and $(CH_2)_3CO_2H$, $C_{1-6}$alkyl substituted by $CONR^{10}SO_2R^{15}$ such as $CH_2CONHSO_2CH_3$ and $CH_2CONHSO_2C_6H_5$, $C_{1-6}$alkyl substituted by phenyl, $Y-R^8$ and $CO-Z-(CH_2)_q-R^{12}$.

In one preferred sub-group of compounds according to the invention $R^5$ represents H; and most aptly $R^6$ and $R^7$ also both represent H.

In one preferred sub-group of compounds according to the invention, $R^3$ represents H or $C_{1-6}$alkyl, more preferably H.

In a further preferred sub-group of compounds according to the invention $R^3$ represents $Y-R^8$.

A yet further preferred sub-group of compounds according to the invention is represented by compounds wherein $R^3$ is $CO-Z-(CH_2)_q-R^{12}$.

A particularly suitable group $R^4$ is the $CH_2OH$ group.

In a further preferred sub-group of compounds of the formula (I), X represents O.

In a further preferred sub-group of compounds of the formula (I), X represents $NR^{19}$ wherein $R^{19}$ is hydrogen or methyl and is preferably hydrogen.

A particularly suitable sub-class of compounds of the formula (I) are those of formula (Ia) and salts thereof:

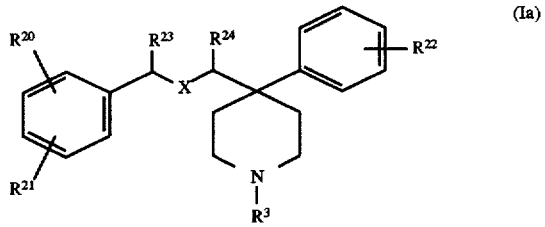

(Ia)

wherein $R^3$ and X are as defined for formula (I);

$R^{20}$ and $R^{21}$ independently represent H, $C_{1-6}$alkyl, $C_{2-6}$alkenyl, $C_{2-6}$alkynyl, $C_{3-6}$cycloalkyl, $C_{3-6}$cycloalkyl $C_{1-4}$alkyl, halo, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $COR^a$, $CO_2R^a$ or $CONR^aR^b$, where $R^a$ and $R^b$ are as previously defined;

$R^{22}$ represents H or halo, preferably H or fluoro; and $R^{23}$ is $C_{1-6}$alkyl substituted by a hydroxy group, preferably $CH_2OH$.

$R^{24}$ is H or methyl.

Most aptly p is 1.

Most aptly X is O or NH.

Specific compounds within the scope of the invention include:

4-phenyl-4-((1-(3,5-bis(trifluoromethyl)phenyl)-2-hydroxyethoxy)methyl) piperidine;

4-phenyl-4-((1-(3,5-bis(trifluoromethyl)phenyl)-2-methoxyethoxy)methyl) piperidine;

4-phenyl-4-((1-(3,5-bis(trifluoromethyl)phenyl)-2-ethoxyethoxy)methyl) piperidine;

4-phenyl-4-((1-(3,5-bis(trifluoromethyl)phenyl)-2-cyclopropylmethoxyethoxy) methyl)piperidine;

4-phenyl4-( (1-(3,5-bis(trifluoromethyl)phenyl)-2-methoxycarbonyl-methoxyethoxy)methyl)piperidine;

4-phenyl-4-((1-(3,5-bis(trifluoromethyl)phenyl)-2-acetoxyethoxy)methyl) piperidine;

5[(4-phenyl-4-((1-(3,5-bis(trifluoromethyl)phenyl)-2-hydroxyethoxy)methyl) piperidine-1-yl)methyl]-2,4-dihydro-[1,2,4]-triazol-3-one;

4-phenyl4-((1-(3,5-bis(trifluoromethyl)phenyl)-2-hydroxyethoxy)methyl)-1-(2-(1-pyrrolidinyl)acetamido) piperidine;

methyl 2-(4-phenylpiperidin4-yl)methoxy-2-(3,5-bis (trifluoromethyl)phenyl) acetate;

isopropyl 2-(4-phenylpiperidin-4-yl)methoxy-2-(3,5-bis (trifluoromethyl)phenyl) acetate;

4-phenyl4-[(1-(3,5-bis(trifluoromethyl)phenyl)-2-hydroxy-2-methylpropyloxy) methyl]piperidine;

2-(4-phenylpiperidin-4-yl)methoxy-2-(3, 5-bis (trifluoromethyl)phenyl) acetamide;

4-phenyl-4-[(1-(3,5-bis(trifluoromethyl)phenyl)-2-aminoethoxy)methyl] piperidine;

4-phenyl-4-[(1-(3-fluoro-5-trifluoromethylphenyl )-2-hydroxyethoxy)methyl] piperidine;

5-[4-phenyl-4-[(1-(3-fluoro-5-trifluoromethyl phenyl)-2-hydroxyethoxy)methyl] piperidin-1-ylmethyl]-2,4-dihydro-[1,2,4]-triazol-3-one;

4-phenyl-4-[(1-(3-fluoro-5-trifluoromethylphenyl)-2-hydroxyethoxy)methyl]-1-(2-(pyrrolidinyl)acetamido) piperidine; and pharmaceutically acceptable acid addition salts thereof.

Further preferred compounds within the scope of the present invention include:

4-phenyl4-[(1-(3, 5-bis(trifluoromethyl )phenyl)-2-(3-methylureido)ethoxy) methyl]piperidine;

4-phenyl-4-[(1-(3,5-bis(trifluoromethyl)phenyl)-2-acetamido)methyl]piperidine;

4-phenyl-4-[(1-(3,5-bis(trifluoromethyl)phenyl)-2-methansulphonamido) methyl]piperidine;

4-phenyl4-[(1-(3,5-bis(trifluoromethyl)phenyl)-2-(carbomethoxymethoxy) ethoxy)methyl]piperidine;

4-(4-fluorophenyl)-4-[(1-(3, 5-bis(trifluoromethyl) phenyl)-2-hydroxyethoxy)methyl]-1-(2-(1-pyrrolidinyl) acetamido)piperidine;

(+)-4-(4-fluorophenyl)-4-[(1-(3,5-bis(trifluoromethyl) phenyl )-2-hydroxyethoxy)methyl]-1-(2-(1-pyrrolidinyl) acetamido)piperidine;

4-phenyl-4-[(1-(3,5-bis(trifluoromethyl)phenyl)-1-hydroxymethyl-2-hydroxyethoxy)methyl]piperidine;

5-[(4-phenyl4-((1-(3,5-bis(trifluoromethyl)phenyl)-1-hydroxymethyl-2-hydroxyethoxy)methyl)piperidin-1-ylmethyl]-2,4-dihydro-[1,2,4]-triazol-3-one;

4-phenyl-4-[(1-(3,5-bis(trifluoromethyl)phenyl) cyclopropyloxy)methyl] piperidine;

4-phenyl-4-[(1-(3,5-bis(trifluoromethyl)phenyl) cyclopropyloxy)methyl]-1-(2-(1-pyrrolidinyl)acetamido) piperidine;

4-phenyl-4-[(1-(3,5-bis(trifluoromethyl)phenyl)-1-methyl-2-hydroxyethoxy) methyl]piperidine;

5-[4-phenyl-4-[(1-(3,5-bis(trifluoromethyl)phenyl)-1-methyl-2-hydroxyethoxy) methyl]piperidin-1-yl)methyl]-2, 4-dihydro-[1,2,4]-triazol-3-one; and pharmaceutically acceptable acid addition salts thereof.

For use in medicine, the salts of the compounds of formula (I) will be pharmaceutically acceptable salts. Other salts may, however, be useful in the preparation of the compounds according to the invention (such as the dibenzoyltartrate salts) or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, sulphuric acid, fumaric acid, maleic acid, succinic acid, acetic acid, citric acid, tartaric acid, carbonic acid, phosphoric acid or p-toluenesulphonic acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

Preferred salts of the compounds according to the invention include the hydrochloride and p-toluenesulphonic acid salts.

The invention also provides pharmaceutical compositions comprising one or more compounds of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or topical administration including administration by inhalation or insufflation.

The invention further provides a process for the preparation of a pharmaceutical composition comprising a compound of formula (I), or a salt thereof, and a pharmaceutically acceptable carrier, which process comprises bringing a compound of formula (I), or a salt thereof into association with a pharmaceutically acceptable carrier or excipient.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include anionic agents such as sodium bis-(2-ethylhexyl)sulfosuccinate (docusate sodium), cationic agents, such as alkyltrimethylammonium bromides, (e.g. cetyltrimethylammonium bromide (cetrimide)), and in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion will preferably comprise fat droplets between 0.1 and 1.0 µm, particularly 0.1 and 0.5 µm, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are adminsitered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

For topical administration, for example as a cream, ointment or lotion, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as MS and ALS and other neuropathological disorders such as peripheral neuropathy, for example diabetic and chemotherapy-induced neuropathy, and postherpetic and other neuralgias; small cell carcinomas such as small cell lung cancer; respiratory diseases, particularly those associated with excess mucus secretion such as chronic obstructive airways disease, bronchopneumonia, chronic bronchitis, cystic fibrosis and asthma, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like, ophthalmic conditions associated with cell proliferation such as proliferative vitreoretinopathy; cutaneous diseases such as contact dermatitis, atopic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosus; gastrointestinal (GI) disorders and diseases of the GI tract such as disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, motion, surgery, migraine, and variations in intercranial pressure, in particular, for example, drug or radiation induced emesis or post-operative nausea and vomiting; disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances*, Eds. J. Kucharczyk et al. CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide. Additionally, a compound of formula (I) may be administered in combination with an anti-inflammatory corticosteroid, such as dexamethasone. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. Pharmacol*, (1993) 250, R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (1).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 2 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

The compounds of the formula (I) may be prepared by a process which comprises reacting a compound of the formula (II) with a compound of the formula (III)

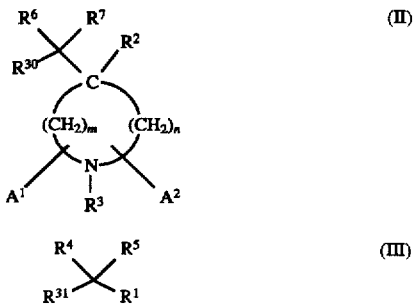

wherein $A^1$, $A^2$, $R^1$, $R^2$, $R^3$, $R^4$, $R^5$, $R^6$, $R^7$, m and n are as defined for formula (I), $R^3$ is as defined for formula (I) except that any reactive moiety $R^3$ or $R^4$ is protected; and one of $R^{30}$ and $R^{31}$ represents a leaving group and the other represents a OH or $NR^{19}$ group where $R^{19}$ is as defined for formula (I); in the presence of base followed by deprotection if required.

Suitably $R^{30}$ represents XH and $R^{31}$ represents a leaving group.

Suitable leaving groups include halo, e.g. chloro, bromo or iodo, or sulphonate derivatives such as tosylate or mesylate.

The reaction is conveniently carried out in a suitable organic solvent, such as an ether, e.g. 1,2-dimethoxyethane, at a temperature in the region of 0° C. Favoured bases of use in the reaction include alkali metal amides and hydrides, such as potassium bis(trimethylsilyl)amide or potassium hydride. Suitably, sodium hydride is used.

Compounds of formula (I) may also be prepared from different compounds of formula (I) by interconversion processes. In particular, interconversion processes may be used to vary the group $R^3$. For example, compounds of formula (I) wherein $R^3$ is other than H may be prepared from the corresponding compounds of formula (I) wherein $R^3$ is H by conventional methods, such as reaction with a compound $R^3$-Hal, where Hal represents halo, in the presence of a base. Suitable reagents and conditions will be readily apparent to those skilled in the art and are illustrated by the accompanying Examples. Suitable bases include organic bases, such as tertiary amines, e.g. triethylamine, and inorganic bases, such as alkali metal carbonates, e.g. sodium carbonate. Compounds of formula (I) wherein $R^3$ is $COR^9$ may also be prepared from compounds of formula (I) wherein $R^3$ is H by, for example, reaction with an appropriate acid anhydride. Compounds of formula (I) wherein $R^3$ is $C_{1-6}$alkyl may be prepared from corresponding compounds of formula (I) wherein $R^3$ is $COR^9$ by reduction using, for example, borane or a borohydride such as sodium cyanoborohydride. Suitable procedures will be readily apparent to those skilled in the art. Compounds of formula (I) wherein $R^3$ is $C_{1-6}$alkyl substituted by $CONR^{10}R^{11}$ may be prepared from corresponding compounds of formula (I) wherein $R^3$ is $C_{1-6}$alkyl substituted by $CO_2R^{10}$ by treatment with ammonia or an amine of formula $NR^{10}R^{11}$ The intermediates of formula (II) above wherein $R^{30}$ is $NR^{16}$ may be prepared from the corresponding intermediates of formula (II) wherein $R^{30}$ represents OH.

Intermediates of formula (II) above wherein $R^{30}$ is OH and $R^6$ and $R^7$ both represent H may be prepared from corresponding compounds of formula (IV)

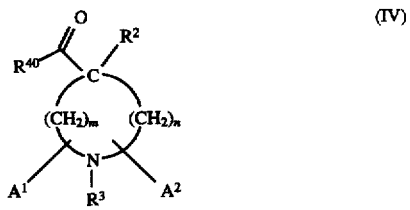

wherein $A^1$, $A^2$, $R^2$, $R^3$, m and n are as defined for formula (II) above and $R^{40}$ represents hydroxy or alkoxy by reduction. Suitable reducing agents will be readily apparent to one skilled in the art and include, for example, metallic hydrides, such as lithium aluminium hydride.

Intermediates of formula (II) wherein $R^{30}$ is OH and one of $R^6$ and $R^7$ is $C_{1-6}$alkyl and the other of $R^6$ and $R^7$ is H may be prepared from compounds of formula (IV) wherein $R^{40}$ is H, by reaction with a Grignard reagent of formula $MgHalR^6$ or $MgHalR^7$, wherein $R^6$ and $R^7$ are as previously defined and Hal is halo such as chloro, bromo or iodo. Intermediates of formula (II) wherein $R^{30}$ is OH and both of $R^6$ and $R^7$ represent $C_{1-6}$alkyl may be prepared from compounds of formula (IV) wherein $R^{40}$ is alkoxy by reaction with Grignard reagents of formulae $MgHalR^6$ and $MgHalR^7$, as above defined. Suitable reaction conditions will be readily apparent to those skilled in the art.

Compounds of formula (IV) wherein $R^{40}$ is H may be prepared from compounds of formula (IV) wherein $R^{40}$ is alkoxy by reduction. Suitable reducing agents will be readily apparent to those skilled in the art and include, for example, where $R^{40}$ is alkoxy, diisobutylaluminium hydride.

Intermediates of formula (II) wherein $R^{30}$ is a leaving group may be prepared from compounds of formula (II) wherein $R^{30}$ is OH, for example, by reaction with a thionyl halide, a mesyl halide or a tosyl halide.

Where they are not commercially available, the intermediates of formula (III) above may be prepared by the procedures described in the accompanying Examples or by alternative procedures which will be readily apparent to one skilled in the art.

Compounds of formula (IV) are commercially available, or may be prepared by known procedures.

For example, suitable methods for the preparation of compounds of formula (IV) are described in European Patent Application no. 0 337 167, *J. Am. Chem. Soc.*, 81, 1201 (1959), *J. Med. Chem.*, 17, 453 (1974) and *J. Med. Chem.*, 24, 218 (1981).

In general, compounds of formula (IV) wherein $R^3$ is H, $R^{40}$ is alkoxy and n is 1 or 2 may be prepared by cyclisation of an intermediate of formula (V)

wherein $R^2$, $R^{40}$, n and m are as previously defined, and Hal represents halo, for example, chloro or bromo, in the presence of a reducing agent such as hydrogen in the presence of a catalyst such as platinum oxide or palladium on charcoal. The reaction is conveniently effected in a suitable organic solvent, such as an ether, for example, tetrahydrofuran.

Analogous methods may be used to produce compounds of the formula (IV) substituted by $A^1$ and $A^2$ wherein $A^1$ and $A^2$ are as defined in relation to formula (II).

Intermediates of formula (V) may be prepared by reaction of compounds of formula (VI) with compounds of formula (VII)

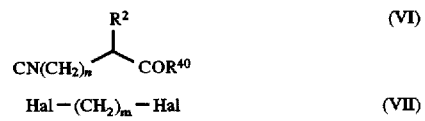

wherein $R^2$, $R^{40}$, n, m and Hal are as previously defined, in the presence of a base. Analogues of the compounds of formula (V) containing groups $A^1$ and $A^2$ as previously defined may be prepared in analogous manner.

Suitable bases of use in the reaction include alkali metal hydrides, such as, for example, sodium hydride. The reaction is conveniently effected in a suitable organic solvent, such as an ether, for example, tetrahydrofuran, suitably at elevated temperature, such as the reflux temperature of the chosen solvent.

Compounds of formulae (VI) and (VII) are commercially available, or may be prepared from commercially available starting materials using conventional procedures well known to those skilled in the art.

Compounds of formula (IV) wherein $R^{40}$ is alkoxy and n is other than zero may in general be prepared from the corresponding compounds of formula (VIII)

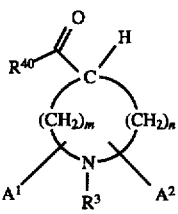

(VIII)

wherein $A^1$, $A^2$, $R^3$, $R^{40}$ and m are as previously defined and n is 1 or 2 by treatment with a base and reaction of the resulting nucleophile with a reagent suitable to introduce the group $R^2$, such as an activated aryl moiety, for example:

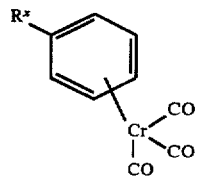

wherein $R^x$ is H or halo, such as chloro; an aryliodide in the presence of nickel bromide (*J. Am. Chem. Soc.*, 99, 4833 (1977)); or a hypervalent aryliodide (*Synthesis*, 709 (1984)).

Compounds of formula (VIII) may be prepared from the corresponding intermediates of formula (IX)

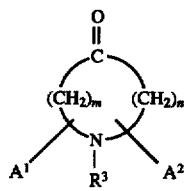

wherein $A^1$, $A^2$, $R^3$, m and n are as defined for formula (VII) by conventional methods, for example, by sequential reaction with lithio-2-trimethylsilyl-1,3-dithiane and an alcohol of formula $R^{40}H$, where $R^{40}$ is alkoxy, in the presence of an acid, such as a mineral acid, for example, hydrochloric acid.

Still further procedures suitable for the preparation of compounds of formula (IV) will be readily apparent to those skilled in the art.

Compounds of the formula (I) wherein $R^3$ and $R^5$ are hydrogen may also be prepared from a corresponding compound of the formula (X):

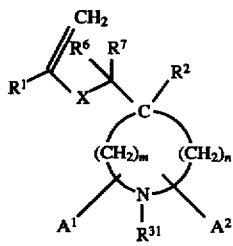

(X)

wherein $A^1$, $A^2$, $R^1$, $R^2$, $R^6$, $R^7$, X, m and n are as defined in relation to formula (I), and $R^{31}$ is a protecting group and any reactive group is protected, by conventional processes followed by deprotection if required.

Most aptly the compound of the formula (X) is one in which $R^{31}$ represents a protecting group such as t-butoxycarbonyl.

Similarly, for compounds of the formula (X) in which X is not oxygen, X preferably represents a protected amino group, such as a t-butoxycarbonyl protected amino group.

Thus for example for compounds wherein $R^4$ is $CH_2OH$, the compound of the formula (X) may be treated with a borane such as $BH_3$, in a suitable solvent such as tetrahydrofuran, followed by treatment with a peroxide, for example hydrogen peroxide, in the presence of a base, such as sodium hydroxide.

Compounds wherein $R^4$ is $CH_2OH$ may be converted into compounds wherein $R^4$ is $(CH_2)_pOR^{16}$ where p is 1 and $R^{16}$ is as defined in relation to formula (I) by reaction with a halide of the formula $R^{16}Hal$, where Hal is as previously defined, in the presence of a suitable base such as sodium hydride.

A group of particularly suitable intermediates may be represented by formula (XI):

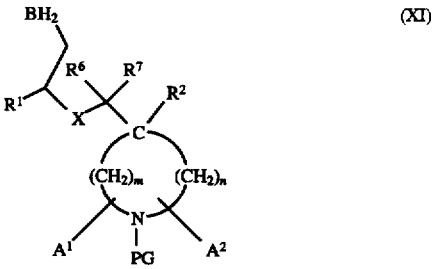

(XI)

wherein $R^1$ $R^2$, $R^6$, $R^7$, X, n and m are as defined in relation to formula (I) and PG represents a protecting group and in particular t-butoxycarbonyl.

The $CH_2BH_2$ moiety may be converted into $R^4$ groups by known methods.

Compounds of the formula (I) wherein $R^3$ and $R^5$ are hydrogen, X is O or S and $R^4$ is a $CO_2R^{16}$ group can be prepared by reaction of a compound of the formula (XII) with one of formula (XIII):

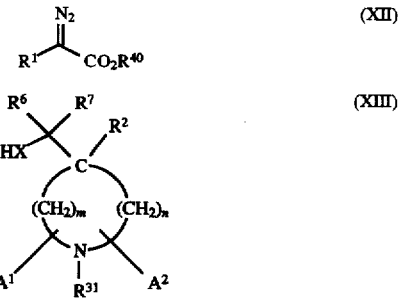

wherein $A^1$, $A^2$, $R^1$, $R^2$, $R^6$, $R^7$, m and n are as defined in relation to formula (I), X is O or S, $R^{31}$ is a protecting group and $R^{40}$ is a $C_{1-6}$alkyl group or a readily removable group. The reaction is effected in the presence of a catalyst such as rhodium(II)acetate in a suitable solvent, for example, a hydrocarbon such as toluene at elevated temperature, conveniently at reflux. Thereafter, $R^{31}$ may be replaced by H and, if desired, the readily removable ester may be replaced by H or a salting ion in conventional manner. The $CO_2R^{40}$ group may also be converted to other $R^4$ groups by known methods.

Another group of particularly useful intermediates may be represented by formula (XIV):

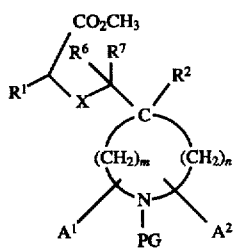

(XIV)

wherein $R^1$, $R^2$, $R^6$, $R^7$, X, n and m are as defined in relation to formula (I) and PG represents a protecting group and in particular t-butoxycarbonyl.

The $CO_2CH_3$ moiety may be converted into other $R^4$ groups by known methods. Thus, for example, reaction with a Grignard reagent of formula $R^cMgHal$ where $R^c$ is an alkyl group and Hal is as previously defined will give compounds where $R^4$ is a tertiary alcohol. Secondary alcohols may be prepared firstly by reduction of the ester moiety to an aldehyde using, for example, diisobutylaluminium hydride, followed by reaction with either $R^cLi$ or $R^cMgHal$.

The aldehyde may also be used as a precursor for alkenyl intermediates where the group at position $R^4$ has the formula —CH=CHR$^d$, where $R^d$ is $(CH_2)_sNR^{10}R^{11}$, $(CH_2)_sCO_2R^{16}$, $(CH_2)_sCONR^{10}R^{11}$ or $(CH_2)_sNR^{10}COR^{18}$ (where s is 0, 1 or 2 and $R^{10}$, $R^{11}$ and $R^{18}$ are as previously defined). These compounds may be prepared by a Wittig reaction using, for example, $Ph_3P=CHR^d$ or $(EtO)_3P(O)=CHR^d$. These alkenyl intermediates may be reduced using, for example, catalytic hydrogenation to give compounds wherein $R^4$ is $(CH_2)_pNR^{10}R^{11}$, $(CH_2)_pCO_2R^{16}$, $(CH_2)_p CONR^{10}R^{11}$ or $(CH_2)_pNR^{10}COR^{18}$ and p is 2 to 4.

Compounds wherein $R^4$ is $CONR^{10}R^{11}$ may be prepared by the reaction of a compound of formula (XIV) with an amine of the formula $HNR^{10}R^{11}$ by known methods. Subsequent reduction using, for example, borane in tetrahydrofuran may be used to give a compound wherein $R^4$ is $(CH_2)_pNR^{10}R^{11}$ in which p is 1. Where one or both of $R^{10}$ and $R^{11}$ in the resultant amine is a hydrogen atom, the amine may be further converted into a compound wherein $R^4$ is $(CH_2)_pNR^{10}COR^{18}$ by reaction with, for example, an acyl chloride of the formula $R^{16}COCl$ by known methods.

If a compound of the formula (I) is required in which $R^5$ is an alkyl group it may be prepared via a corresponding compound of the formula (I) in which $R^4$ is $CO_2R^{40}$ group by reaction with KHMDS and an alkyl iodide, followed if desired by replacement of a readily removable group $R^{40}$ by H or a salting ion. The $CO_2R^{40}$ may also be converted to other $R^4$ groups by known methods.

Intermediates of formula (II) wherein $R^{30}$ is $NR^{19}$ and $R^6$ and $R^7$ are hydrogen may be prepared by reduction of a corresponding compound of the formula (XV):

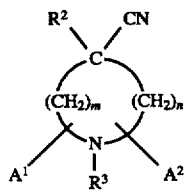

(XV)

wherein $R^2$, $R^3$, $A^1$, $A^2$, n and m are as defined in relation to formula (II).

The reduction may be effected using a reducing agent such as lithium aluminium hydride in order to produce a compound in which $R^{19}$ is hydrogen (which in general is preferred). This may be followed by reductive amination to produce a compound in which $R^{19}$ is a $C_{1-4}$alkyl group in conventional manner.

Compounds of the formula (XV) can be prepared from the corresponding halo compound by reaction with, for example, KCN using known methods. Such halo compounds are either commercially available or may be prepared in an analogous manner to commercial compounds.

Intermediates of formula (II) wherein $R^{30}$ is OH and $R^6$ and $R^7$ are hydrogen have the general formula (XVI):

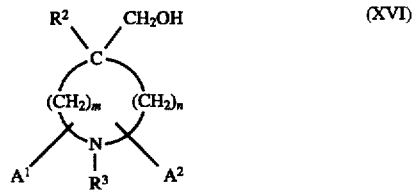

(XVI)

wherein $A^1$, $A^2$, $R^2$, $R^3$, n and m are as defined in relation to formula (I). These compounds may be prepared by reduction of a corresponding compound of the formula (XVII):

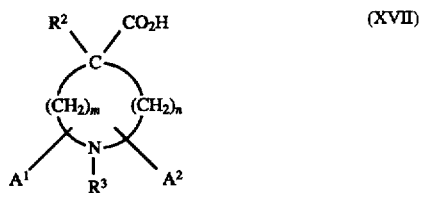

(XVII)

using lithium aluminium hydride in conventional manner. Most aptly the reduction is performed on a compound of the formula (XVI) in which $R^3$ is hydrogen. After reduction $R^3$ is aptly replaced by a t-butoxycarbonyl group which acts as a favoured protecting group.

Compounds of the formula (XVII) wherein $R^3$ is hydrogen may be obtained commercially or prepared in an analogous manner to commercial compounds.

Compounds of formula (X) may be prepared from a corresponding compound in which the =CH$_2$ moiety is an =O group, by reaction with dimethyltitanocene in toluene according to the method of N. A. Petasis et al, *J. Am. Chem. Soc.*, (1990) 112(17), 6392. Alternatively, titanium tetrachloride/zinc dust/tetrahydrofuran/dichloromethane may be used according to the method of P. Kocienski and M. Mortimore, Tet. Lett., (1988) 29(27), 3375. When X is an oxygen atom, this ester precursor may be prepared by conventional methodology from an alcohol of formula (XVI) and an appropriate benzoic acid derivative in the presence of a suitable coupling agent such as 1-(3-dimethylaminopropyl)-3-ethylcarbodiimide hydrochloride and a base such as 4-dimethylaminopyridine. The reaction is conveniently effected in a solvent such as dimethylformamide.

It will be appreciated that a mixture of diastereomers may be resolved by methods known in the art. Thus, for example, an intermediate of formula (XIV) may be resolved by the preparation of a chiral auxiliary using, for instance, (R)-4-benzyl-2-oxazolidone. Following resolution by, for example, chromatography, the oxazolidone moiety may be removed using a reducing agent such as lithium borohydride to yield compounds wherein $R^4$ is $CH_2OH$ and $R^5$ is H. The less favoured diastereomer may be isomerised to give a further mixture of diastereomers and the resolution procedure repeated.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the NK1 receptor of less than 150 nM.

The compounds of this invention may be formulated as specifically illustrated at pages 35 to 36 of International Patent Specification No. WO 93/01165.

The following non-limiting examples serve to illustrate the present invention:

EXAMPLE 1

4-Phenyl-4-((1-(3,5-bis(trifluoromethyl)phenyl)-2-hydroxyethoxy)methyl) piperidine Hydrochloride a) 1-tert-Butoxycarbonyl-4-phenyl-4-hydroxymethyl piperidine 4-Phenyl-4-carboxy piperidine tosylate (10 g) was added portionwise to a solution of lithium aluminium hydride (1.52 g) in dry tetrahydrofuran (100 ml) at 0° C. After addition was complete the reaction mixture was warmed to reflux for 30 minutes and then allowed to cool to room temperature. The reaction was then quenched by addition of 2N sodium hydroxide solution until a white granular precipitate formed. The mixture was filtered and the filtrate extracted with ethyl acetate (200 ml), dried ($MgSO_4$), filtered and solvent removed to afford a clear oil. The residual oil was taken up in dichloromethane (50 ml) and di-tert-butyl-dicarbonate (1.9 g) added. The resulting mixture was stirred at room temperature for 18 hours. The solvent was removed and the residual oil subjected to chromatography on silica gel to afford the title compound as a colourless oil. $^1$H NMR (360 MHz, $CDCl_3$) δ 1.43 (9H, s), 1.75 (2H, td, J=11.0, 10 Hz), 2.17 (2H, m), 3.05 (2H, td, J=11.0, 1.0 Hz), 3.55 (2H, s), 3.73 (2H, m), 7.24–7.41 (5H, m); MS ($Cl^+$) 292 $(M+H)^+$.

b) 1-tert-Butoxycarbonyl-4-phenyl-4-[3,5-bis (trifluoromethyl) benzoyloxymethyl]piperidine 1-(3-Dimethylaminopropyl)-3-ethyl-carbodiimide hydrochloride (897 mg) was added to a stirred solution of 3,5-bis(trifluoromethyl) benzoic acid (292 mg) and 4-dimethylaminopyridine (483 mg) in dry dimethylformamide (20 ml). The resulting solution was stirred for 30 minutes then the compound of step (a) above (1.0 g) was added. The resulting solution was stirred at room temperature for 19 hours. At this time the reaction was diluted with water (200 ml) and extracted into ethyl acetate. The organic layers were separated, washed with water, brine, and dried over $MgSO_4$. Filtration and removal of solvent under reduced pressure afforded a yellow oil. Purification by chromatography on silica gel (20% ethyl acetate/n-hexane) afforded the product as a clear oil. $^1$H NMR (360 MHz, $CDCl_3$) δ 1.4 (9H, s), 1.95 (2H, m), 2.3 (2H, m), 3.03 (2H, m), 3.8 (2H, m), 4.35 (2H, s), 7.0–7.2 (5H, m), 8.01 (1H, s), 8.25 (2H, s).

c) 1-tert-Butoxycarbonyl-4-phenyl-4-[1-(3,5-bis (trifluoromethyl)phenyl) vinyloxymethyl]piperidine Titanium tetrachloride (1.06 g) was added to cooled (0° C.) stirred tetrahydrofuran under a dry nitrogen atmosphere. After the exotherm had subsided the solution was allowed to warm to room temperature and tetramethylethylene diamine (1.69 g) added followed 15 minutes later by freshly activated zinc dust (819 mg). The resulting mixture was stirred for 30 minutes at room temperature at which point dibromomethane (0.21 ml) and the compound of step (b) above (716 mg) were added. The reaction was allowed to proceed for 18 hours at room temperature. After this time the reaction was quenched with saturated $K_2CO_3$ (7 ml) and diluted with diethyl ether. The resulting black suspension was filtered through a plug of grade III neutral alumina, eluting with 1% triethylamine/diethyl ether. The filtrate was dried over $MgSO_4$, filtered and the solvent removed under reduced pressure. The residual oil was purified by chromatography on silica gel (10% ethyl acetate/n-hexane) to afford the title compound. $^1$H NMR (360 MHz, $CDCl_3$) δ 1.2 (9H, s), 1.95 (2H, m), 2.38 (2H, m), 3.05 (2H, m), 3.8 (2H, s), 3.95 (2H, m), 4.21 (1H, d, J=1.0 Hz), 4.63 (1H, d, J=1.0 Hz), 7.1–7.3 (5H, m), 7.7 (1H, s), 7.76 (2H, s).

d) 1-tert-Butoxycarbonyl-4-phenyl-4-((1-(3,5-bis (trifluoromethyl)phenyl)-2-hydroxyethoxy)methyl) piperidine The compound of step (c) above was treated with $BH_3$.tetrahydrofuran (5 ml of a 1M solution in tetrahydrofuran) under an atmosphere of nitrogen for 2 hours. A mixture of 4N NaOH (10 ml) and $H_2O_2$ (5 ml of a 29% solution in water) was added and the reaction stirred for 3 hours, then extracted with diethyl ether. The ethereal extracts were washed with sodium bisulphite solution then dried ($Na_2SO_4$) and concentrated. The residue was purified by chromatography on silica gel eluting with ethyl acetate-petroleum ether (3:7) to give the title compound as a colourless oil.

e) 4-Phenyl-4-((1-(3,5-bis(trifluoromethyl)phenyl)-2-hydroxyethoxy) methyl)piperidine Hydrochloride The compound of step (d) above was dissolved in methanolic hydrogen chloride for 2 hours then concentrated and triturated with diethyl ether and filtered to give the title compound as a white solid, m.p. 198°–202° C.

Analysis Calcd. for $C_{22}H_{23}F_6NO_2.HCl.0.5H_2O$: C, 53.61; H, 5.11; N, 7.84; Found: C, 53.92; H, 4.84; N, 7.85.

EXAMPLE 2

4-Phenyl-4-((1-(3,5-bis(trifluoromethyl)phenyl)-2-methoxyethoxy)methyl) piperidine Hydrochloride The compound of Example 1(d) above (200 mg) in dimethoxyethane (1 ml) was stirred with sodium hydride (60% in oil, 100 mg) for one hour. Iodomethane (0.5 ml) was added and the reaction was stirred for 16 hours and then poured into water, extracted with ethyl acetate, and washed with aqueous sodium chloride. The organic layer was dried ($MgSO_4$), filtered and evaporated. The residue was purified by chromatography on silica using ethyl acetate/petroleum ether (1:4) to yield an oil which was dissolved in ethereal hydrogen chloride and stirred for 16 hours. The solvent was removed to yield the title compound. $^1$H NMR (360 MHz, $d_6$-DMSO) δ 7.98 (1H, s), 7.72 (2H, s), 7.41–7.26 (5H, m), 4.65 (1H, t, J=4.7 Hz), 3.53–3.16 (6H, m), 3.20 (3H, s), 2.81–2.69 (2H, m), 2.47–2.33 (2H, m), 2.23–2.02 (2H, m). MS ($Cl^+$) 462 $(M+H)^+$.

EXAMPLE 3

4-Phenyl-4-((1-(3,5-bis(trifluoromethyl)phenyl)-2-ethoxyethoxy)methyl) piperidine Hydrochloride This was prepared in a similar manner to Example 2 using the compound of Example 1(d) and iodoethane. $^1$H NMR (360 MHz, $d_6$-DMSO) δ 7.97 (1H, s), 7.72 (2H, s), 7.41–7.10 (5H, m), 4.63 (1H, t, J=4.7 Hz), 3.55–3.29 (6H, m), 3.28–3.10 (2H, m), 2.75–2.65 (2H, m), 2.38–2.24 (2H, m), 2.14–2.00 (2H, m), 1.00 (3H, t, J=7.2 Hz). MS ($Cl^+$) 476 $(M+H)^+$.

EXAMPLE 4

4-Phenyl-4-((1-(3,5-bis(trifluoromethyl)phenyl)-2-cyclopropylmethoxyethoxy) methyl)piperidine Hydrochloride

This was prepared in a similar manner to Example 2 using the compound of Example 1 (d) and cyclopropyl methyl bromide. $^1$H NMR (360MHz, $d_6$-DMSO) δ 7.91 (1H, s), 7.66 (2H, s), 7.35–7.19 (5H, m), 4.58 (1H, t, J=4.7 Hz), 3.50–3.06 (6H, m), 2.76–2.61 (2H, m), 2.33–2.17 (2H, m), 2.08–1.94 (2H, m), 0.84–0.77 (1H, m), 0.36–0.30 (2H, m), 0.01–0.06 (2H, m). MS (CI+) 502 (M+H)$^+$.

EXAMPLE 5

4-Phenyl-4-((1-(3,5-bis(trifluoromethyl)phenyl)-2-methoxycarbonylmethoxy ethoxy)methyl)piperidine Hydrochloride

This was prepared in a similar manner as Example 2 using the compound of Example 1 (d) and methyl bromoacetate. $^1$H NMR (360 MHz, $d_6$-DMSO) δ7.98 (1H, s), 7.75 (2H, s), 7.41–7.24 (5H, m), 4.68 (1H, t, J=5 Hz), 4.11 (2H, s), 3.62 (3H, s), 3.69–3.30 (4H, m), 3.29–3.10 (2H, m), 2.78–2.60 (2H, m), 2.39–2.00 (4H, m). MS (Cl$^+$) 520 (M+H)$^+$.

EXAMPLE 6

4-Phenyl4-((1-(3,5-bis(trifluoromethyl)phenyl)-2-acetoxyethoxy)methyl) piperidine Hydrochloride

The compound of Example 1(d) (1.2 g) was dissolved in dichloromethane (50 ml) and treated with triethylamine (0.5 ml) and acetylchloride (0.5 ml). The reaction was stirred for 16 hours, poured into citric acid and washed with brine, saturated sodium bicarbonate solution, dried (MgSO$_4$) filtered and evaporated to yield an oil which was purified by chromatography on silica gel using ethyl acetate/petroleum ether (1:4) to yield an oil. This was dissolved in dry ethereal hydrogen chloride and stirred for 2 hours. The solvent was removed to yield the title compound. $^1$H NMR (360MHz, $d_6$-DMSO) δ 8.01 (1H, s), 7.74 (2H, s), 7.40–7.27 (5H, m), 4.74 (1H, t, J=3.6 Hz), 4.16 (2H, d, J=3.6 Hz), 3.53–3.31 (1H, m), 3.30–3.14 (2H, m), 2.80–2.70 (2H, m), 2.5 (3H, s), 2.35–2.20 (2H, m), 2.19–1.92 (2H, m). MS (Cl$^+$) 490 (M+H)$^+$ Analysis Calcd. for C$_{24}$H$_{25}$F$_6$NO$_3$.HCl.H$_2$O: C, 53.00; H, 5.19; N, 2.58; Found C, 53.17; H, 4.97; N, 2.61%.

EXAMPLE 7

5-[(4-Phenyl-4-((1-(3,5-bis(trifluoromethyl)phenyl)-2-hydroxyethoxy) methyl)piperidin-1-ylmethyl]-2,4-dihydro-[1,2,4,]-triazol-3-one

The compound of Example 1 (3.2 g) in dry dimethylformamide (50 ml) was stirred for 2 hours with methoxycarbonyl chloromethyl imidrazone (1.15 g) and potassium carbonate (3.5 g). The mixture was heated to reflux for 2 hours then cooled, diluted with water and extracted with diethyl ether 3 times. The combined extracts were washed with water, dried (Na$_2$SO$_4$) and concentrated to give a residue which was purified by chromatography on silica gel eluting with 10% methanol/dichloromethane to give the title compound as a white solid, mp 105°–106° C.; MS (Cl$^+$) 545 (M+H)$^+$; $^1$H NMR (360 MHz, $d_6$-DMSO) δ 1.84–2.22 (6H, m), 2.42–2.56 (2H, m), 3.23 (1 H, d, J=9 Hz), 3.31 (2H, s), 3.38–3.56 (3H, m), 4.39 (1H, t, J=5.4 Hz), 4.75 (1H, t, J=5.8 Hz), 7.18 (1H, t, J=7 Hz), 7.26–7.37 (4H, m), 7.68 (2H, s) and 7.94 (1 H, s).

EXAMPLE 8

4-Phenyl-4-((1-(3,5-bis(trifluoromethyl)phenyl )-2-hydroxyethoxy)methyl)-1-(2-(1-pyrrolidinyl)acetamido) piperidine Hydrochloride

(1-Pyrrolidinyl)acetic acid (0.68 g) in dry dimethyl formamide (20 ml) was treated with triethylamine (1.38 ml) and cooled to -30° C. iButyl chloroformate (0.55 ml) was added and the reaction stirred for 10 minutes before adding the compound of Example 1 (1.0 g). The solution was allowed to warm slowly to room temperature then stirred for 16 hours. The solution was concentrated under reduced pressure then ethyl acetate was added and washed with aqueous sodium chloride, then dried and concentrated to give an oil which was dissolved in methanol and stirred with potassium carbonate for 1 hour. The solvent was evaporated and the residue partitioned between ethyl acetate and aqueous sodium chloride. The organic solution was dried (Na$_2$SO$_4$) and concentrated to give a residue which was purified by chromatography on neutral alumina eluting with 1% methanol/dichloromethane. The resulting product was treated with ethereal hydrogen chloride to give a white solid which was recrystallised from ethyl acetate to give the title compound; mp 110°–112° C.; MS (Cl$^+$) 559 (M+H)$^+$; $^1$H NMR (360 MHz, $d_6$-DMSO) δ 1.78–2.32 (8H, m), 2.96–3.18 (4H, m), 3.29 (1H, d, J=9.1 Hz), 3.38–3.60 (6H, m), 3.80–3.95 (1H, m), 4.24–4.33 (1 H, m), 4.38– 4.47 (2H, m), 7.23 (1H, t, J=7.5 Hz), 7.34 (2H, t, J=7.5 Hz), 7.41 (2H, t, J=7.5 Hz), 7.68 (1H, s), 7.70 (1H, s) and 7.96 (1H, s).

EXAMPLE 9

Methyl 2-(4-phenylpiperidin-4-yl)methoxy-2-(3,5-bis (trifluoromethyl)phenyl) acetate Hydrochloride a) Methyl 3,5-bis(trifluoromethyl)phenylacetate 3,5-Bis(trifluoromethyl)phenylacetic acid (10.0 ·, 36.7 mmol), was dissolved in methanol (150 ml). The solution was cooled to 4° C. under an atmosphere of dry nitrogen, and thionyl chloride (10 ml) was added dropwise with vigorous stirring over 30 minutes. The mixture was warmed to room temperature, and then stirred for 1 hour. The solvents were evaporated at reduced pressure, the residue dissolved in diethyl ether (150 ml), washed with saturated aqueous NaHCO$_3$, dried (Na$_2$SO$_4$), and evaporated to afford the title compound (10.5 g, 100%), as a colourless oil which was used without further purification.

b) Methyl 2-diazo-2-(3,5-bis(trifluoromethyl)phenyl) acetate

To methyl 3,5-bis(trifluoromethyl)phenylacetate (43.5 g, 160 mmol), in dry acetonitrile (250 ml), cooled to -5° C., was added 2,4,6-triisopropyl benzenesulfonyl azide (52.7 g). To the resulting solution was added 1,8-diazabicyclo[5.4.0] undec-7-ene (25.5 ml), and the mixture was stirred at -5° C. for 1 hour. The mixture was warmed to room temperature, and then stirred for 0.5 hour. The solvents were evaporated at reduced pressure and the residue purified by chromatography on silica gel (eluant 5% diethyl ether/petroleum ether), to afford the the title compound as yellow prisms. LR (film, NaCl) 1740, 2140 cm$^{-1}$.

c) Methyl 2-(1-tert-butoxycarbonyl-4-Phenylpiperidin-4-yl)methoxy-2-(3,5-bis(trifluoromethyl)phenyl)acetate To a solution of the product of Example 1(a) (8.6 g, 30.8 mmol) and rhodium acetate (20 mg) in dry benzene (20 ml) heated at reflux under an atmosphere of dry argon, was added dropwise with stirring over 25 hours, a solution of methyl 2-diazo-2-(3,5-bis(trifluoromethyl)phenyl)acetate (6.13 g, 19.6 mmol) in dry benzene (6 ml), via a syringe pump. The resulting solution was heated for a further 1 hour, cooled to room temperature, and the solvents evaporated at reduced pressure. The residue was purified by chromatography on silica gel (eluant 25% to 40% diethyl ether/ petroleum ether), to afford the the title compound as a colourless oil. $^1$H NMR (250 MHz, CDCl$_3$) δ 7.79 (1H, s), 7.70 (2H, s), 7.40–7.21 (5H, m), 4.67 (1 H, s), 3.77 (2H, m), 3.69 (3H, s), 3.67 (1H, d, J=9 Hz), 3.36 (1H, d, J=9 Hz), 3.04 (2H, m), 2.25 (2H, m), 1.91 (2H, m), 1.44 (9H, s).

d) Methyl 2-(4-phenylpiperidin-4-yl)methoxy-2-(3,5-bis (trifluoromethyl) phenyl)acetate Hydrochloride The product of step (c) above was dissolved in saturated methanolic hydrogen chloride, and allowed to stand at room temperature for 24 hours. The solvents were evaporated at reduced pressure then toluene was added to the residue and evaporated at reduced pressure to afford the title compound as a colourless foam. Analysis Calcd. for C$_{23}$H$_{23}$F$_6$NO$_3$.HCl. 0.5(H$_2$O): C, 53.03; H, 4.84; N, 2.69; Found: C, 52.78; H, 4.75; N, 2.75%. MS (Cl$^+$) 476 (M+H)$^+$.

EXAMPLE 10 iso-Propyl 2-(4-phenylpiperidin-4-yl)methoxy-2-(3,5-bis (trifluoromethyl) phenyl)acetate Hydrochloride The product of Example 9 (0.070 g), was dissolved in propan-2-ol saturated with hydrogen chloride, and allowed to stand at room temperature for 48 hours. The solvents were evaporated at reduced pressure then toluene was added to the residue and evaporated at reduced pressure. The resulting 5 gum was dissolved in acetonitrile (1 ml), water (2 ml) was added, and the solution freeze dried to afford the title compound as a colourless foam.

Analysis Calcd. for C$_{25}$H$_{27}$F$_6$NO$_3$.HCl. 1.5(H$_2$O): C,52.96; H, 5.51; N, 2.4; Found: C, 53.09; H, 5.26; N, 2.41%. MS (Cl$^+$) 504 (M+H)$^+$.

EXAMPLE 11

4-Phenyl-4-[(1-(3,5-bis(trifluoromethul)phenyl)-2-hydroxy-2-methyl-propyloxy)methyl]piperidine Hydrochloride.

To the product of Example 9(c) (0.522 g, 0.9 mmol) dissolved in dry tetrahydrofuran (1 ml) at −78° C. under argon was added a solution of methylmagnesium chloride (1.0 ml of a 3.0M solution in tetrahydrofuran). The mixture was stirred for 2 hours at −78° C. then quenched by addition of saturated aqueous NH$_4$Cl, and warmed to room temperature. The reaction was partitioned between ethyl acetate and water; the organic layer was separated, dried (Na$_2$SO$_4$), and evaporated at reduced pressure. The residue was purified by chromatography on silica gel (eluant 25% to 40% diethyl ether/petroleum ether), to afford a colourless foam (0.318 g). This was dissolved in saturated methanolic hydrogen chloride, and allowed to stand at room temperature for 24 hours. The solvents were evaporated at reduced pressure, and the residue partitioned between saturated aqueous NaHCO$_3$ and ethyl acetate. The organic extracts were dried (Na$_2$SO$_4$) and evaporated at reduced pressure. The residue was purified by chromatography on grade (III) alumina (eluant 2% to 10% methanol/dichloromethane), to afford the the title compound as a colourless oil. 2N Aqueous hydrochloric acid (2 ml), was added followed by acetonitrile to give a homogeneous solution, which was then freeze dried. The resulting gum was dissolved in hot diethyl ether (10 ml), excess petroleum ether was added, and the solvents evaporated at reduced pressure to afford the title compound as a colourless solid.

Analysis Calcd. for C$_{24}$H$_{27}$F$_6$NO$_2$.HCl. 0.5(H$_2$O): C, 55.34; H. 5.61; N. 2.69; Found: C, 55.43; H, 5.70; N, 2.69%. MS (Cl$^+$) 476 (M+H)$^+$.

EXAMPLE 12

2-(4-Phenylpiperidin-4-yl)methoxy-2-(3,5-bis (trifluoromethyl)phenyl) acetamide Hydrochloride Ammonia gas was passed through a solution of the product of Example 9 (0.644 g) in dry methanol (50 ml) at −15° C. until saturated. The reaction flask was sealed with a rubber septum and allowed to stand at room temperature for 48 hours, then solvents were evaporated at reduced pressure. The residue was dissolved in acetonitrile (1 ml) and 2N aqueous hydrochloric acid (2 ml), and the solution freeze dried. The residue was boiled with ethyl acetate, allowed to cool, and the title compound collected by filtration as a colourless solid, mp 146°–148° C. Analysis Calcd. for C$_{22}$H$_{22}$F$_6$N$_2$O$_2$.HCl.H$_2$O: C, 51.32; H, 4.89; N, 5.44; Found: C, 51.28; H, 4.73; N, 5.84%. MS (Cl$^+$) 461 (M+H)$^+$.

EXAMPLE 13

4-Phenyl-4-[(1-(3,5-bis(trifluoromethyl)phenyl)-2-aminoethoxy)methyl] Piperidine Hydrochloride.

Ammonia gas was passed through a solution of the product of Example 9(c) (1.0 g), in dry methanol (50 ml), cooled at −15° C., until saturated. The reaction flask was sealed with a rubber septum, and allowed to stand at room temperature for 48 hours then the solvents were evaporated at reduced pressure. The residue was treated with borane-tetrahydrofuran complex (20 ml of a 1.0M solution in tetrahydrofuran), and heated at reflux for 24 hours. After cooling to room temperature, methanol was added dropwise with caution to destroy excess reagent. The solvents were evaporated at reduced pressure, the residue dissolved in methanol (20 ml), and the solution allowed to stand at room temperature for 24 hours. The residue obtained by evaporation of the methanol at reduced pressure, was purified by chromatography on silica gel (eluant 5% methanol/dichloromethane), to afford the tbutoxycarbonyl-protected piperidine (0.39 g). This was dissolved in saturated ethereal hydrogen chloride (10 ml) and methanol (1 ml) then allowed to stand at room temperature for 48 hours. The title compound was collected as a colourless solid by filtration. Analysis Calcd. for C$_{22}$H$_{24}$F$_6$N$_2$O. $_2$(HCl): C, 50.88; H, 5.05; N, 5.39; Found: C, 50.82; H, 4.98; N, 5.26%. MS (Cl$^+$) 447 (M+H)$^+$.

EXAMPLE 14

(+)-4-Phenyl-4-[(1-(3,5-bis(trifluoromethyl)phenyl)-2-hydroxyethoxy) methyl]piperidine Hydrochloride a) 2-(1-tert-Butoxycarbonyl-4-phenylpiperidine-4-yl) methoxy-2-(3,5-bis(trifluoromethyl)phenyl)acetic acid To a solution of methyl 2-[1(-tert-butoxycarbonyl4-phenylpiperidin4-yl)methoxy]-2-(3,5-bis(trifluoromethyl) phenyl)acetate (11 g, 0.019 mol) in methanol (100 ml) at 0° C. was added potassium hydroxide (3.2 g, 5.7 mmol), followed by water (3 ml). The homogeneous solution was stirred at 0° C. for 1 hour. The methanol was removed in vacuo and pH4 buffer (100 ml) added to the residue. The product was extracted into diethyl ether (2×100 ml), the combined ethereal solutions dried (MgSO$_4$), filtered and evaporated in vacuo. The resulting white foam was used without further purification.

b) (4R)-3-[2-(1-tert-Butoxycarbonyl-4-phenylpiperidine4-yl)methoxy-2-(3,5-bis(trifluoromethyl) phenyl)acetyl]-4-benzyl-2-oxazolidinone The compound of step (a) above (1.0 g, 1.7 mmol) was dissolved in anhydrous dichloromethane (50 ml). Dimethylformamide(0.05 ml) was added followed by oxalyl chloride (0.2 ml, 2.3 mmol) dropwise. After stirring at 25° C. for 0.5 hours the solvent was removed in vacuo. The resulting residue was azeotroped with toluene (2×50 ml)

then, as a solution in anhydrous toluene (5 ml), added at −78° C. to the lithium anion of (4R)-4-benzyl-2-oxazolidinone (generated by adding n-BuLi (1.1 ml, 1.6M, 1.7 mmol) to a solution of (4R)-(+)-4-benzyl-2-oxazolidinone (0.301 g, 1.7 mmol) in tetrahydrofuran (5 ml) at −78° C.). The resulting colorless solution was stirred at −78° C. for a further 0.75 hours and quenched by addition of saturated ammonium chloride solution (30 ml). The product was extracted into ethyl acetate (2×30 ml) then the organic layer was dried over $MgSO_4$ and filtered. The clear oil obtained after removal of solvent in vacuo was purified by chromatography on silica gel eluting first with 20% ethyl acetate/hexane to obtain the title compound, diastereomer A (0.350 g), and then with 30% ethyl acetate/hexane to obtain the title compound, diastereomer B (0.380 g). Diastereomer A was converted to a mixture (1:2) of diastereomer A and diastereomer B by treating a solution in dichloromethane with anhydrous triethylamine for 16 hours. The solvents were evaporated and the mixture separated by chromatography as described above to obtain diastereomer B: $^1$H NMR (250 MHz, $CDCl_3$) δ 7.78 (s, 1H), 7.70 (s, 2H), 7.10–7.30 (m, 8H), 6.88 (m, 2H), 5.86 (s, 1H), 4.62 (m, 1H), 4.06–4.12 (m, 2H), 3.68 (m, 2H), 3.54 (d, J=7 Hz, 1 H), 3.22 ( d, J=7 Hz, 1 H), 2.96 (m, 3H), 2.54 ( dd, J=7, 2 Hz, 1H), 2.1 (m, 2H), 1.8 (m, 2H), 1.34 (s, 9H).

c) (+)1 -tert-Butoxycarbonyl-4-phenyl-4-( 1-(3,5-bis (trifluoromethyl) phenyl)-2-hydroxyethoxy)methyl/piperidine The product of step (b), diastereomer B above (1.8 g, 2.5 mmol), was dissolved in diethyl ether (50 ml) and cooled to 0° C. under a nitrogen atmosphere. Water (0.05 ml, 2.75 mmol) was added, followed by lithium borohydride (0.054 g, 2.5 mmol). The reaction was stirred at 0° C. for another 0.75 hours and quenched by addition of 1N NaOH (50 ml). The mixture was extracted with ethyl acetate (2×100 ml), the organic solutions washed with brine, dried ($MgSO_4$), filtered and evaporated in vacuo. The residue was purified by chromatography on silica gel eluting with 20% ethyl acetate/hexane to obtain the title compound as a white foam:$^1$H NMR (250 MHz, $CDCl_3$) δ 7.68 (1H, s), 7.44 (2H, s), 7.15–7.34 (5H, m), 4.23 (1H, dd, J=3 Hz), 3.68 (2H, m), 3.44 (2H, br d, J=7 Hz), 3.30 (2H, dd, J=7 Hz), 2.96 (2H, m), 2.14 (2H, m), 1.74 (2H, m), 1.32 (9H, s).

d) (+)4-Phenyl-4-[(1-(3,5-bis(trifluoromethyl)phenyl)-2-hydroxyethoxy) methyl]piperidine Hydrochloride The compound of step (c) above (1.15 g) was dissolved in ethereal hydrogen chloride for 24 hours. The solvent was removed under reduced pressure to afford the title compound: $^1$H NMR(360 MHz, $d_6$-DMSO) δ 1.94–2.20 (4H, m), 2.6–2.8 (2H, m), 3.0–3.25 (2H, m), 3.29 (2H, s), 4.40 (2H, m), 4.80 (1 H, t, J=10.5 Hz), 7.10–7.30 (5H, m), 7.60 (2H, s), 7.95 (1H, s).

EXAMPLE 15

(−)-4-Phenyl-4-[(1-(3,5-bis(trifluoromethyl)phenyl)-2-hydroxyethoxy)methyl]Piperidine Hydrochloride Prepared by the methods of Examples 14(c) and 14(d) using the compound of Example 14(b), diastereomer A.

EXAMPLE 16

(+)-5-[4-Phenyl-4-[(1-(3,5-bis(trifluoromethyl)phenyl)-2-hydroxyethoxy)methyl]piperidin-1-ylmethyl]-2,4-dihydro-[1,2,4]-triazol-3-one a) N-Methoxycarbonyl chloromethyl imidrazone Sodium methoxide (400 mg) was added to a stirred solution of chloroacetonitrile (20 g) in dry methanol (120 ml). The resulting solution was stirred for 1 hour at room temperature, and then neutralised by the addition of acetic acid. Methyl carbazate (23.6 g) was then added and stirring continued for 1 hour. The solvent was then removed under reduced pressure and the residue taken up in ethyl acetate, washed with water and the organic layers separated and dried over $MgSO_4$. Filtration and removal of solvent afforded a white solid. Recrystallisation from isopropanol afforded the title compound as white needles, mp=45°–49° C.; $^1$H NMR(360 MHz, $CDCl_3$) δ 1.3 (3H ,s), 4.00 (2H, s), 5.5 (2H, br s), 8.8 (1 H, br s).

b) (+)-5-[4-Phenyl-4-[(1-(3,5-bis(trifluoromethyl)phenyl) -2-hydroxyethoxy) methyl]piperidin-1-ylmethyl]2,4-dihydro-[1,2,4]-triazol-3-one N-Methoxycarbonyl chloromethyl imidrazone (356 mg) was added to a stirred suspension of the compound of Example 14 (961 mg) and $K_2CO_3$ (1.19 g) in dry dimethylformamide at 0° C. The resulting solution was warmed to room temperature and stirred for two hours, then filtered through celite. The clear filtrate was then warmed to 150° C. for 3 hours, cooled to room temperature, diluted with water and extracted into diethyl ether. The organic layers were separated and dried over $MgSO_4$, filtered and the solvent removed under reduced pressure. The product was was purified by chromatography on silica gel (10% methanol/dichloromethane) to give the title compound as a white solid. $^1$H NMR (360 MHz, $CDCl_3$) δ 2.22–2.31 (6H, m), 2.78 (2H, m), 3.22 (1H, d, J=11.0 Hz), 3.28 (1H, d, J=11.0 Hz), 3.39 (2H, s), 3.56 (2H, m), 4.37 (1H, t, J=4.0 Hz), 7.20–7.30 (5H, m), 7.58 (2H, s), 7.75 (1H, s); MS ($Cl^+$) 545 $[M+1]^+$; $[α]_D^{20}$=+42.8° C. (c=1dichloromethane).

EXAMPLE 17

(+)-4-Phenyl4-[(1-(3,5-bis(trifluoromethyl)phenyl)-2-hydroxyethoxy)methyl]-1-(2-(pyrrolidinyl)acetamido) piperidine Hydrochloride 1-[3-Dimethylaminopropyl]-3-ethylcarbodiimide hydrochloride (797 mg), hydroxybenzo-triazole trihydrate (475 mg) and triethylamine (0.890 ml) were added to a stirred solution of 2-pyrrolidinyl acetic acid hydrochloride (528 mg) in dry dimethylformamide at room temperature. After 30 minutes a solution of the compound of Example 14 (800 mg) in dry dimethylformamide was added, followed by triethylamine (0.590 ml). The resulting solution was stirred at room temperature for 4 hours. The reaction was quenched with water and extracted into diethyl ether then the organic solution was dried ($MgSO_4$) and evaporated to give a yellow oil. The residue was purified by chromatography on grade 3 neutral alumina (1% methanol/dichloromethane) then treated with ethereal hydrogen chloride to afford the title compound, mp=106°–108° C.;

Analysis Calcd. for $C_{28}H_{32}F_6N_2O_3 \cdot HCl \cdot 0.5H_2O$: C, 55.68; H, 5.67; N, 4.64. Found: C, 55.87; H, 5.65; N, 4.51%. $^1$H NMR of free base (360 MHz, $CDCl_3$), δ 1.76 (4H, m,), 1.80–1.86 (2H, m), 2.30 (2H, m), 2.55 (4H, m), 2.99 (2H, m), 3.40 (2H, s), 3.51 (2H, s), 3.56 (2H, m), 3.84 (2H, m), 4.30 (1H, t, J=10 Hz), 7.20–7.38 (5H, m), 7.67 (I H, s), 7.77 (1H, s), 7.94 (1 H, s). MS ($Cl^+$) 559 $[M+1]^+$.

EXAMPLE 18

(+)-4-Phenyl-4-[(1-(3-fluoro-5-trifluoromethylphenyl)-2-hydroxyethoxy) methyl]piperidine Hydrochloride Prepared by the method of Examples 9 and 14 using (3-fluoro-5-trifluoromethylphenyl)acetic acid. $^1$H NMR (360 MHz, $d_6$-DMSO) δ 2.04–2.29 (4H, m), 2.67–2.80 (2H, m), 3.18–3.27 (2H, m), 3.37 (2H, s), 4.34 (1H, t, J=4.5 Hz), 7.06–7.51 (8H, m).

EXAMPLE 19
(+)-5-[4-Phenyl-4-[(1-(3-fluoro-5-trifluoromethylphenyl)-2-hydroxyethoxy) methyl]piperidin-1-ylmethyl]-2,4-dihydro-[1,2,4]-triazol-3-one Prepared by the method of Example 16 from the compound of Example 18. $^1$H NMR (360 MHz, CDCl$_3$) δ 2.17–2.31 (6H, m), 2.78 (2H, m), 3.19 (1H, d, J=10 Hz), 3.32 (1H, d, J=10 Hz), 3.39 (2H, s), 3.51 (2H, m), 4.30 (1H, t, J=4.0 Hz), 6.97–7.34 (8H, m).

EXAMPLE 20
(+)4-Phenyl-4-[(1-(3-fluoro-5-trifluoromethylphenyl)-2-hydroxyethoxy) methyl]-1-(2-(pyrrolidinyl)acetamido) piperidine Hydrochloride Prepared by the method of Example 17 from the compound of Example 18. $^1$H NMR of free base (360 MHz, CDCl$_3$) δ 1.79 (6H, m), 2.20 (2H, m), 2.53 (4H, m), 2.90 (2H, m), 3.22 (2H, m), 3.32–3.42 (4H, m), 3.71 (2H, m), 4.15 (1H, t, J=3.0 Hz), 6.80–7.30 (8H, m).

EXAMPLE 21
4-Phenyl-4-[(1 -(3,5-bis(trifluoromethyl)phenyl)-2-(3-methylureido)ethoxy) methyl]piperidine Hydrochloride Methyl isocyanate (33 μl, 0.56 mM) was added to a solution of the compound of Example 13 (300 mg, 0.56 mM) in dichloromethane (5 ml). The reaction was stirred at room temperature for 16 h. Dichloromethane (10 ml) was added and the solution was washed with water (2×20 ml) and dried over sodium sulphate. Removal of the solvent in vacuo left an oil which was chromatographed on silica eluting with 50% ethyl acetate/petrol to give a white solid. This was taken up in diethyl ether (5 ml) and treated with ethereal HCl (5 ml). The solution was left to stand for 16 h and the solvent was removed to give the title compound as a white foam. MS (Cl$^+$) 504 [M+H]$^+$.

Analysis Calcd. for C$_{24}$H$_{27}$N$_3$O$_2$F$_6$. HCl. H$_2$O: C, 51.66; H, 5.42; N, 7.53; Found: C, 51.58; H, 5.30; N, 7.16%.

EXAMPLE 22
4-Phenyl-4-[(1-(3,5-bis(trifluoromethyl)phenyl)-2-(acetamido)ethoxy)methyl]Piperidine Hydrochloride Acetic anhydride (53 μl, 0.56 mM) was added to a solution of the compound of Example 13 (300 mg, 0.56 mM) in dichloromethane (5 ml) containing N,N-dimethylaminopyridine (69 mg, 0.56 mM). The reaction was stirred for 16 h, and purified as for Example 21 to give the title compound as a white crystalline solid. m.p. 138°–140° C., MS (Cl$^+$) 489 [M+H]$^+$.

EXAMPLE 23
4-Phenyl-4-[(1-(3,5-bis(trifluoromethyl)phenyl)-2-(methansulphonamido) ethoxy)methyl]piperidine Hydrochloride Triethylamine (78 μl, 0.56 mM) was added to a solution of the compound of Example 13 (300 mg, 0.56 mM) in dichloromethane (5 ml). Methanesulphonyl chloride (43 μl, 0.56 mM) was added and the solution was stirred for 16 h at room temperature. Dichloromethane (10 ml) was added and the solution was washed with water (2×20 ml) and dried over sodium sulphate. Removal of the solvent left an oil which was purified and treated with ethereal HCl as in Example 21, giving the title compound as a white foam (50 mg). MS (Cl$^+$) 525[M+H]$^+$. $^1$H NMR (360 MHz, d$_6$-DMSO) δ 1.98–2.24 (4H, m), 2.70–2.90 (2H, m), 2.79 (3H, s), 3.10–3.42 (6H, m), 3.54–3.59 (1H, m), 4.51–4.59 (1H, m), 7.01–7.06 (1 H, m), 7.24–7.45 (4H, m), 7.67 (2H, s), 7.99 (1 H, s), 8.49 (1 H. br s).

EXAMPLE 24
4-Phenyl-4-[(1-(3,5-bis(trifluoromethyl)phenyl)-2-(carbomethoxymethoxy) ethoxy)methyl]piperidine Hydrochloride Prepared from the compound of Example 1 (d) by the method of Example 2, using methyl bromoacetate in place of methyl iodide. $^1$H NMR (360 MHz, d$_6$-DMSO) δ 2.00–2.12 (2H, m), 2.24–2.35 (2H, m), 2.62–2.77 (2H, m), 3.17 (2H, br m), 3.29 (1H, d, J=6.0 Hz), 3.62 (3H, s+m), 4.01 (2H, s), 4.08 (1 H, t, J=6.0 Hz), 7.24–7.41 (5H, m), 7.68 (2H, s), 7.97 (1 H, s). MS (EI$^+$) 520 (M+H$^+$).

EXAMPLE 25
4-(4-Fluorophenyl)-4-[(1-(3,5-bis(trifluoromethyl)phenyl)-2-hydroxyethoxy) methyl]-1-(2-(1-pyrrolidinyl)acetamido) piperidine Hydrochloride a) Methyl 4-fluorophenylacetate 4-Fluorophenyl acetic acid (25 g) was dissolved in anhydrous methanol, stirred under nitrogen and cooled in an ice/methanol bath. Dry HCl gas was bubbled through the reaction for 1 hr. The methanol was removed by rotary evaporator and the residue was dispersed between aqueous sodium hydrogen carbonate and dichloromethane. The organic layer was washed with brine, dried (MgSO$_4$) and concentrated to afford the title compound as a clear oil (24.4 g). $^1$H NMR (360 MHz, CDCl$_3$) δ 3.61 (2H, s), 3.70 (3H, s), 6.97–7.06 (2H, m), 7.20–7.27 (2H, m). MS Cl$^+$169 [M+H]$^+$.

b) 4-(4-Fluorophenyl)-4-carbomethoxy-1-methylpiperidine

Methyl 4-fluorophenylacetate (24.4 g) was dissolved in dry dimethyl sulphoxide (150 ml) and added dropwise to sodium hydride (15.7 g of an 80% dispersion in oil) under nitrogen. After 20 minutes mechlorethamine hydrochloride (24 g) in dry dimethyl sulphoxide (125 ml) was added over a period of 20 minutes. The reaction was poured onto ice (200 ml) and left overnight. The mixture was extracted with diethyl ether (50×250 ml) and the combined organic solutions were extracted with 5N HCl (100 ml). The aqueous solution was treated with potassium carbonate and extracted with ethyl acetate (3×250 ml). The combined organic extracts were dried (MgSO$_4$) and concentrated in vacuo to afford a brown oil. The oil was purified by flash chromatography eluting with ethyl acetate graduated to 8% methanol in ethyl acetate, to afford the title compound (9.5 g). $^1$H NMR (360 MHz, CDCl$_3$) δ 1.9–2.03 (2H, m), 2.07–2.19 (2H, m), 2.27 (3H, s), 2.51–2.62 (2H, m), 2.72–2.86 (2H, m), 3.65 (3H, s), 6.98–7.06 (2H, m), 7.27–7.39 (2H, m). MS (Cl$^+$) 224 [M+H]$^+$.

c) 4-(4-Fluorophenyl)-4-hydroxymethyl-1-tert-butoxycarbonylpiperidine 4-(4-(Fluorophenyl-4-carbomethoxy-1-methylpiperidine (19.2 g) in 1,2-dichloroethane (400 ml) at 5° C. was treated with chloroethylchloroformate (23.4 ml) for 15 minutes. The solution was heated under reflux for 12 hours then cooled and concentrated under reduced pressure. The residual oil was dissolved in methanol (600 ml) and heated under reflux for 3 hours then cooled and concentrated. The residue in tetrahydrofuran (225 ml) at 0° C. was treated with lithium aluminium hydride (108.5 ml of a 1.0M solution in tetrahydrofuran) and, after 10 minutes, the solution was heated under reflux for 3 hours. The reaction was cooled then quenched by addition of water (4.1 ml), 15% sodium hydroxide (4.1 ml) and water (12.1 ml). Di-tert-butyl dicarbonate (18.9 g) in dichloromethane (250 ml) was added and the mixture was stirred for 16 hours then filtered through sodium sulphate. The solution was concentrated and the residue purified by chromatography on silica gel eluting with hexane/ethyl acetate (3:2) to give the title compound as a white solid, MS (Cl$^+$) 310 [M+H]$^+$.

d) 4-(4-Fluorophenyl)-4-[(1-(3,5-bis(trifluoromethyl) phenyl)-2-hydroxyethoxy)methyl]-1-(2-(1-pyrrolidinyl) acetamido)piperidine hydrochloride Prepared from 4-(4-fluorophenyl)4-hydroxymethyl-1-tert-butoxycarbonyl piperidine using the methods described in Examples 1 and 8. m.p. 128°–131° C.; Analysis Calcd. for $C_{18}H_{31}F_7N_2O_3$. HCl. $H_2O$: C 53.29; H, 5.43; N, 4.44; Found: C, 53.41; H, 5.47; N, 4.30%.

EXAMPLE 26
(+)-4-(4-Fluorophenyl)4-[(1-(3,5-bis(trifluoromethyl) phenyl)-2-hydroxyethoxy)methyl]-1-(2-(1-pyrrolidinyl) acetamido)piperidine Hydrochloride.

Prepared from 4-(4-fluorophenyl )-4-hydroxymethyl-1-tert-butoxycarbonylpiperidine by the methods detailed in Examples 9, 14 and 17. m.p. 134°–136° C.; Analysis Calcd. for $C_{18}H_{31}F_6N_2O_3$. HCl: C, 54.86; H, 5.26; N, 4.56; Found: C, 54.48; H, 4.96; N, 4.72%.

EXAMPLE 27
4-Phenyl-4-[(1-(3,5-bis(trifluoromethyl)phenyl)-1-hydroxymethyl-2-hydroxyethoxy)methyl]piperidine Hydrochloride (a) 1-tert-Butoxycarbonyl-4-phenyl-4-[(1-(3,5-bis (trifluoromethyl)phenyl)-2-benzyloxy-1-methoxycarbonylethoxy)methyl]piperidine Diisopropylamine (0.63 ml, 4.5 mmol) was added to degassed anhydrous tetrahydrofuran and the flask cooled to 0° C. n-Butyl lithium (1.6M in hexanes, 2.8 ml, 4.5 mmol) was added dropwise, the solution stirred for a further 10 minutes and cooled to –78° C. The compound of Example 9(c) (2.0 g, 3.5 mmol) was azeotroped with toluene and dissolved in anhydrous tetrahydrofuran (15 ml). The solution was degassed with nitrogen for 5 minutes and added dropwise to the freshly prepared lithium diisopropylamine and stirred for a further 30 minutes. The anion was then quenched with benzyloxychloromethyl ether (0.63 ml, 4.5 mmol), stirred for a further 10 minutes and warmed to 0° C. for a further 1 h. Saturated aqueous ammonium chloride solution (50 ml) was added and the product extracted into ethyl acetate (2×75ml). The combined organic layers were dried over (MgSO$_4$) and removed in vacuo. The residue was chromatographed on silica eluting with 15% ethyl acetate/ petroleum ether to give a colourless oil. $^1$H NMR (CDCl$_3$) δ 7.76 (1H, s), 7.73 (2H, s), 7.23–7.37 (8H, m), 7.09 (2H, m), 4.40 (2H, dd), 3.82 (2H, dd), 3.65 (3H, s), 3.73 (2H, dt), 3.56 (1 H, d), 3.40 (1 H, d), 3.09 (br t, 2H), 2.21 (2H, br m), 1.89 (2H, m), 1.44 (9H, s).

b) 4-Phenyl-4-[(1-(3,5-bis(trifluoromethyl)Phenyl)-1-hydroxymethyl-2-hydroxyethoxy)methyl]piperidine Hydrochloride The oil from step (a) above was dissolved in anhydrous tetrahydrofuran (50 ml) and lithium borohydride (0.140 g, 6.5 mmol) was added. The reaction was stirred at 25° C. for 30 minutes and quenched with saturated aqueous ammonium chloride solution (75 ml) and extracted into ethyl acetate (75 ml). The organic layer was dried over (MgSO$_4$) and removed in vacuo. The residue was dissolved in ethanol (15 ml) and hydrogenated at 50 psi over Pd(OH)$_2$ (0.150 g) for 16 h. The catalyst was filtered and the solvent evaporated. The residue was chromatographed on silica eluting with ethyl acetate. The oil obtained was treated with ethereal HCl and left standing for 16 h. The solid formed was filtered off and washed with ether to obtain the title compound. $^1$H NMR (DMSO-d6) δ 7.99 (1 H, s), 7.75 (2H, s), 7.48 (4H, m), 7.35 (1H, m), 3.85 (4H, s), 3.47 (2H, s), 3.33 (2H, br d), 2.97 (2H, br t), 2.56 (2H, br d), 2.10 (2H, br t). MS (Cl$^+$) 478 [M+H]$^+$.

EXAMPLE 28
5-[(4-Phenyl-4-((1-(3,5-bis(trifluoromethyl)phenyl)-1-hydroxymethyl-2-hydroxyethoxy)methyl)piperidin-1-ylmethyl]-2,4-dihydro-[1,2,4]-triazol-3-one Prepared from the compound of Example 27, by the method described in Example 7, m.p. 148°–150° C., MS (Cl)$^+$575 [M+H]$^+$.

EXAMPLE 29
4-Phenyl-4-[(1-(3,5-bis(trifluoromethyl)phenyl) cyclopropyloxy)methyl]piperidine Hydrochloride The compound of Example 1 (c) (0.500 g, 0.922 mmol) was dissolved in anhydrous ether (10 ml) and diethylzinc (1.0M solution in hexanes, 1.84 ml, 1.84 mmol) was added. The solution was cooled to 0° C. and diiodomethane (0.15 ml 1.84 mmol) was added. The reaction was diluted with ethyl acetate (50 ml) and washed with saturated aqueous ammonium chloride solution. The organic layer was dried over (MgSO$_4$) and evaporated. The residue was purified by chromatography on silica eluting with 5% ethyl acetate/ hexanes→10% ethyl acetate/hexanes. The product obtained was left standing in HCl/ether for 16 h. The solvent was removed in vacuo and the title compound suspended in ether and filtered. $^1$H NMR (DMSO-d$_6$) δ 7.90 (1H, s), 7.50 (2H, s), 7.29–7.40 (5H, m), 3.36 (2H, s), 3.17 (2H, m), 2.74 (2H, m), 2.30 (2H, m), 2.01 (2H, m), 1.13 (4H, m). MS (Cl$^+$) 444 [M+H]$^+$.

EXAMPLE 30
4-Phenyl-4-[(1-(3,5-bis(trifluoromethyl)phenyl) cyclopropyloxy)methyl]-1-(2-(1-pyrrolidinyl)acetamido) piperidine Hydrochloride Prepared from the compound of Example 29 by the method of Example 8; m.p. 158°–160° C. $^1$H NMR (DMSO-d$_6$) δ 7.90 (1H, s), 7.52 (2H, s), 7.34–7.51 (4H, m), 7.28 (1H, m), 4.32 (2H, dd), 3.84 (1H, m), 3.38 (7H, m), 3.04 (2H), 2.16 (2H), 1.78–1.99 (m, 6H).

EXAMPLE 31
4-Phenyl-4-[(1-(3,5-bis(trifluoromethyl)phenyl)-1-methyl-2-hydroxyethoxy) methyl]piperidine Hydrochloride (a) tert-Butoxycarbonyl-4-phenyl4-[(1-(3,5-bis (trifluoromethyl)phenyl)-1-methyl-2-methoxycarbonylethoxy)methyl]piperidine Diisopropylamine (0.37 ml, 2.80 mmol) was added to de-gassed tetrahydrofuran (10 ml) and the solution cooled to 0° C. n-Butyl lithium (1.6M in hexanes, 1.7 ml, 2.80 mmol) was added and the reaction stirred for 10 minutes. The lithium diisopropylamine solution was cooled to –78° C. and the compound of Example 9(c) (1.1 g, 0.19 mmol, as a solution in de-gassed tetrahydrofuran) added dropwise. The yellow anion was stirred for 40 minutes before addition of methyl iodide (0.17 ml, 0.280 mmol) dropwise. The reaction was stirred at –78° C. for 1 h, and quenched with aqueous ammonium chloride and allowed to warm to room temperature. The product was extracted into ethyl acetate (50 ml) and the organic layer dried (MgSO$_4$) and evaporated. The residue was chromatographed on silica eluting with 15% ethyl acetate/hexanes to give the title compound as a colourless oil. $^1$H NMR (CDCl$_3$) δ 7.76 (3H, s), 7.35 (4H, m), 7.26 (1H, m), 3.80 (2H, m), 3.76 (3H, s), 3.47 (1H, d), 3.36 (1H, d), 3.05 (2H, m), 2.20–2.37 (2H, m), 1.86–1.91 (2H, m), 1.58 (3H, s), 1.44 (9H, s).

(b) 4-Phenyl-4-[(1-(3,5-bis(trifluoromethyl)phenyl)-1-methyl-2-hydroxyethoxy)methyl]piperidine Hydrochloride The oil from step (a) above (0.66 g) was dissolved in tetrahydrofuran (8 ml) and lithium borohydride (0.082 g, 3.3 mmol) added and the reaction stirred for 3 h. The reaction mixture was concentrated in vacuo and saturated aqueous ammonium chloride added carefully. The product was extracted into ethyl acetate (2×25 ml), the combined organic layers dried (MgSO$_4$) and evaporated. The residue was dissolved in ethereal HCl and after 10 minutes at 25° C., the solvent removed in vacuo. The resulting white solid was filtered and washed with ether to give the title compound. $^1$H NMR (DMSO-d$_6$) δ 7.82 (1H, s), 7.75 (2H, s), 7.38–7.45 (4H, m), 7.32 (1H, m), 3.57 (2H, s), 3.46 (1H, d), 3.30 (2H, m (under H$_2$O peak)), 3.20 (1H, d), 2.94 (2H, m), 2.55 (2H, m), 2.15 (2H, m), 1.48 (3H, s). MS (Cl$^+$) 462 [M+H]$^+$.

EXAMPLE 32

5-[4-Phenyl-4-[(1-(3,5-bis(trifluoromethyl)phenyl)-1-methyl-2-hydroxyethoxy) methyl]piperidin-1-yl)methyl]-2, 4-dihydro-[1,2,4]-triazol-3-one Prepared by the method described in Example 7 from the compound of Example 31. m.p. 142°–144° C. MS (Cl$^+$) 559 [M+H]$^+$.

EXAMPLE 33

4-Phenyl-4-[(1-(3,5-bis(trifluoromethyl)phenyl)-1-methyl-2-hydroxyethoxy) methyl]-1-(2-(1-pyrrolidinyl)acetamido) piperidine Hydrochloride Prepared by the method described in Example 8 from the compound of Example 31. $^1$H NMR (DMSO-d$_6$) δ 7.94 (1H, s), 7.73 (2H, d), 7.43 (2H, d), 7.36 (2H, t), 7.26 (1H, t), 4.79 (1H, dd), 4.39 (1H, d), 4.25 (1H, d), 3.88 (1H, m), 3.47 (6H, m), 3.22 (2H, m), 3.07 (2H, m), 2.17 (2H, m), 1.92 (6H, m), 1.39 (3H, s). MS (Cl$^+$) 573 [M+H]$^+$.

We claim:

1. A compound of the formula (I) or a pharmaceutically acceptable salt thereof:

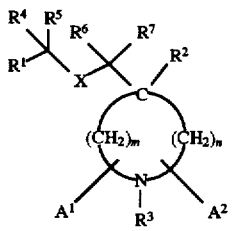

wherein

A$^1$ and A$^2$ each independently represent hydrogen or C$_{1-4}$alkyl;

m is 2, 3 or 4;

n is zero when m is 4; n is 1 when m is 3 and n is 2 when m is 2;

R$^1$ represents phenyl optionally substituted by 1, 2 or 3 groups selected from C$_{1-6}$alkyl, C$_{2-6}$alkenyl, C$_{2-6}$alkynyl, C$_{3-6}$cycloalkyl, C$_{3-6}$cycloalkylC$_{1-4}$alkyl, halo, cyano, nitro, trifluoromethyl, trimethylsilyl, —OR$^a$, —SR$^a$, —SOR$^a$, —SO$_2$R$^a$, —NR$^a$R$^b$, —NR$^a$COR$^b$, —NR$^a$CO$_2$R$^b$, —COR$^a$, —CO$_2$R$^a$ or —CONR$^a$R$^b$, where R$^a$ and R$^b$ each independently represent H, C$_{1-6}$alkyl, phenyl or trifluoromethyl;

R$^2$ represents phenyl optionally substituted by 1, 2 or 3 groups selected from C$_{1-6}$alkyl, C$_{2-6}$alkenyl, C$_{2-6}$alkynyl, C$_{3-6}$cycloalkyl, C$_{3-6}$cycloalkylC$_{1-4}$alkyl, halo, cyano, nitro, trifluoromethyl, trimethylsilyl, —OR$^a$, —SR$^a$, —SOR$^a$, —SO$_2$R$^a$, —NR$^a$R$^b$, —NR$^a$COR$^b$, —NR$^a$CO$_2$R$^b$, —CO$_2$R$^a$ or —CONR$^a$R$^b$, where R$^a$ and R$^b$ are as previously defined; heteroaryl selected from indazolyl, thienyl, furyl, pyridyl, thiazolyl, tetrazolyl and quinolyl; ben-zhydryl; or benzyl; wherein each heteroaryl and each phenyl moiety of benzyl and benzhydryl may be substituted by C$_{1-6}$alkyl, C$_{3-6}$cycloalkyl, C$_{3-6}$cycloalkyl C$_{1-4}$alkyl, C$_{1-6}$alkoxy, halo or trifluoromethyl;

R$^3$ represents H, COR$^9$, CO$_2$R$^{10}$, COCONR$^{10}$R$^{11}$, COCO$_2$R$^{10}$, SO$_2$R$^{15}$, CONR$^{10}$SO$_2$R$^{15}$, C$_{1-6}$alkyl optionally substituted by a group selected from (CO$_2$R$^{10}$, CONR$^{10}$R$^{11}$, hydroxy, cyano, COR$^9$, NR$^{10}$R$^{11}$, C(NOH)NR$^{10}$R$^{11}$, CONHphenyl(C$_{1-4}$alkyl), COCO$_2$R$^{10}$, COCONR$^{10}$R$^{11}$, SO$_2$R$^{15}$, CONR$^{10}$SO$_2$R$^{15}$ and phenyl optionally substituted by 1, 2 or 3 substituents selected from C$_{1-6}$alkyl, C$_{3-6}$cycloalkyl, C$_{3-6}$cycloalkylC$_{1-4}$alkyl, C$_{1-6}$alkoxy, halo and trifluoromethyl), Y—R$^8$ or CO—Z—(CH$^2$)$_q$—R$^{12}$;

R$^4$ represents C$_{1-6}$alkyl substituted by a hydroxy group, or (CH$_2$)$_p$NR$^{10}$R$^{11}$, CO$_2$R$^{16}$, CONR$^{10}$R$^{11}$, (CH$_2$)$_p$CO$_2$R$^{16}$, (CH$_2$)$_p$CONR$^{10}$R$^{11}$, (CH$_2$)$_p$NR$^{10}$OCOR$^{18}$, (CH$_2$)$_p$NR$^{10}$SO$_2$R$^{15}$ (CH$_2$)$_p$OR$^{16}$, (CH$_2$)$_p$OC(O)R$^{10}$ or (CH$_2$)$_p$O(CH$_2$)$_r$COR$^{17}$;

R$^5$ represents hydrogen or C$_{1-6}$alkyl optionally substituted by a hydroxy group, or (CH$_2$)$_p$NR$^{10}$R$^{11}$, CO$_2$R$^{16}$, CONR$^{10}$R$^{11}$, (CH$_2$)$_p$CO$_2$R$^{16}$, (CH$_2$)$_p$CONR$^{10}$OR$^{11}$, (CH$_2$)$_p$NR$^{10}$COR$^{18}$, (CH$_2$)$_p$NR$^{10}$SO$_2$R$^{15}$, (CH$_2$)$_p$OR$^{16}$, (CH$_2$)$_p$OC(O)R$^{10}$or (CH$_2$)$_p$O(CH$_2$)$_r$COR$^{17}$;

or R$^4$ and R$^5$ together with the carbon atom to which they are attached form a C$_{3-6}$cycloalkyl ring which may be substituted by 1 or 2 groups selected from C$_{1-6}$alkyl, C$_{1-6}$alkoxy, hydroxy or C$_{1-6}$alkyl substituted by hydroxy;

R$^6$ and R$^7$ each independently represent H or C$_{1-6}$alkyl;

R$^8$ represents an optionally substituted aromatic heterocycle;

R$^9$ represents H, C$_{1-6}$alkyl, C$_{3-6}$cycloalkyl, C$_{3-6}$cycloalkylC$_{1-4}$alkyl, or phenyl;

R$^{10}$ and R$^{11}$ each independently represent H or C$_{1-6}$alkyl;

R$^{12}$ represents NR$^{13}$R$^{14}$ or an optionally substituted aromatic or non-aromatic azacyclic or azabicyclic group;

R$^{13}$ and R$^{14}$ each independently represent H, C$_{1-6}$alkyl, phenyl optionally substituted by 1, 2 or 3 groups selected from C$_{1-6}$-alkyl, C$_{1-6}$alkoxy, halo or trifluoromethyl, or phenylC$_{1-4}$alkyl optionally substituted in the phenyl ring by 1, 2 or 3 groups selected from C$_{1-6}$alkyl, C$_{1-6}$alkoxy, halo or trifluoromethyl;

R$^{15}$ represents C$^{16}$alkyl, trifluoromethyl or phenyl optionally substituted by 1, 2 or 3 substituents selected from C$_{1-6}$alkyl, C$_{1-6}$alkoxy, halo and trifluoromethyl;

R$^{16}$ represents C$_{1-6}$alkyl;

R$^{17}$ represents C$_{1-6}$alkoxy, amino, C$_{1-4}$alkylamino or di(C$_{1-4}$alkyl)amino;

R$^{18}$ represents C$_{1-6}$alkyl, NR$^{13}$R$^{14}$ or an optionally substituted aromatic or non-aromatic azacyclic or azabicyclic group;

X represents O or NR$^{19}$ where R$^{19}$ represents hydrogen or C$_{1-6}$alkyl;

Y represents a hydrocarbon chain of 1, 2, 3 or 4 carbon atoms which may optionally be substituted by oxo;

Z represents CH$_2$, O, S or NR$^{10}$;

p represents an integer from 1 to 4;

q represents zero or an integer from 1 to 6; and r represents an integer from 1 to 4.

2. A compound as claimed in claim 1 wherein A$^1$ and A$^2$ each independently represent hydrogen or C$_{1-4}$alkyl;

m is 2, 3 or 4;

n is zero when m is 4; n is 1 when m is 3 and n is 2 when m is 2;

$R^1$ represents phenyl optionally substituted by 1, 2 or 3 groups selected from $C_{1-6}$alkyl, $C_{2-6}$alkenyl, $C_{2-6}$alkynyl, $C_{3-6}$cycloalkyl, $C_{3-6}$cycloalkyl$C_{1-4}$alkyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$COR^a$, —$CO_2R^a$ or —$CONR^aR^b$, where $R^a$ and $R^b$ each independently represent H, $C_{1-6}$alkyl, phenyl or trifluoromethyl;

$R^2$ represents phenyl optionally substituted by 1, 2 or 3 groups selected from $C_{1-6}$alkyl, $C_{2-6}$alkenyl, $C_{2-6}$alkynyl, $C_{3-6}$cycloalkyl, $C_{3-6}$cycloalkyl$C_{1-4}$alkyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$CO_2R^a$ or —$CONR^aR^b$, where $R^a$ and $R^b$ are as previously defined; heteroaryl selected from indazolyl, thienyl, furyl, pyridyl, thiazolyl, tetrazolyl and quinolyl; benzhydryl; or benzyl; wherein each heteroaryl and each phenyl moiety of benzyl and benzhydryl may be substituted by $C_{1-6}$alkyl, $C_{3-6}$cycloalkyl, $C_{3-6}$cycloalkyl$C_{1-4}$alkyl, $C_{1-6}$alkoxy, halo or trifluoromethyl;

$R^3$ represents H, $COR^9$, $CO_2R^{10}$ $COCONR^{10}R^{11}$, $COCO_2R^{10}$, $SO_2R^{15}$, $CONR^{10}SO_2R^{15}$, $C_{1-6}$alkyl optionally substituted by a group selected from ($CO_2R^{10}$, $CONR^{10}R^{11}$, hydroxy, cyano, $COR^9$, $NR^{10}R^{11}$ C(NOH)$NR^{10}R^{11}$, CONHphenyl($C_{1-4}$alkyl), $COCO_2R^{10}$, $COCONR^{10}R^{11}$, $SO_2R^{15}$, $CONR^{10}SO_2R^{15}$ and phenyl optionally substituted by 1, 2 or 3 substituents selected from $C_{1-6}$alkyl, $C_{3-6}$cycloalkyl, $C_{3-6}$cycloalkyl$C_{1-4}$alkyl, $C_{1-6}$alkoxy, halo and trifluoromethyl), Y—$R^8$ or CO—Z—$(CH_2)_q$—$R^{12}$;

$R^4$ is $C_{1-6}$alkyl substituted by a hydroxy group, or $(CH_2)_p$$NR^{10}R^{11}$, $CO_2R^{16}$, $CONR^{10}R^{11}$, $(CH_2)_pCO_2R^{16}$, $(CH_2)_pCONR^{10}R^{11}$, $(CH_2)_pNR^{10}COR^{16}$, $(CH_2)_p$$NHSO_2R^{12}$, $(CH_2)_pOR^{16}$, $(CH_2)_pOC(O)R^{10}$ or $(CH_2)_p$$O(CH_2)_rCOR^{17}$;

$R^5$, $R^6$ and $R^7$ each independently represent H or $C_{1-6}$alkyl;

$R^8$ represents an optionally substituted aromatic heterocycle;

$R^9$ represents H, $C_{1-6}$alkyl, $C_{3-6}$cycloalkyl, $C_{3-6}$cycloalkyl$C_{1-4}$alkyl, or phenyl;

$R^{10}$ and $R^{11}$ each independently represent H or C-alkyl;

$R^{12}$ represents $NR^{13}R^{14}$ or an optionally substituted aromatic or non-aromatic azacyclic or azabicyclic group;

$R^{13}$ and $R^{14}$ each independently represent H, $C_{1-6}$alkyl, phenyl optionally substituted by one or more of $C_{1-6}$alkyl, $C_{1-6}$alkoxy, halo or trifluoromethyl or phenyl$C_{1-4}$alkyl optionally substituted in the phenyl ring by 1, 2 or 3 groups selected from $C_{1-6}$alkyl, $C_{1-6}$alkoxy, halo or trifluoromethyl;

$R^{15}$ represents $C_{1-6}$alkyl, trifluoromethyl or phenyl optionally substituted by 1, 2 or 3 substituents selected from $C_{1-6}$alkyl, $C_{1-6}$alkoxy, halo and trifluoromethyl;

$R^{16}$ represents $C_{1-6}$alkyl;

$R^{17}$ represents $C_{1-6}$alkoxy, amino, $C_{1-4}$alkylamino or di($C_{1-4}$alkyl)amino;

Y represents a hydrocarbon chain of 1,2,3 or 4 carbon atoms which may optionally be substituted by oxo;

Z represents $CH_2$, O, S or $NR^{10}$;

p represents 1 to 4;

q represents zero, 1, 2, 3, 4, 5 or 6;

r represents 1 to 4;

X represents O or $NR^{19}$ where $R^{19}$ represents hydrogen or $C_{1-6}$alkyl; or a pharmaceutically acceptable salt thereof.

3. A compound as claimed in claim 1 wherein $A^1$ and $A^2$ each independently represent hydrogen or $C_{1-4}$ alkyl;

m is 2, 3 or 4;

n is zero when m is 4; n is 1 when m is 3 and n is 2 when m is 2;

$R^1$ represents phenyl optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, —$OR^a$, —$SR^a$, —$SOR^a$, $S_2R^a$, —$NR^aR^b$, —$NR^aCOR^b$, —$NR^aCO_2R^b$, —$COR^a$, —$CO_2R^a$ or —$CONR^aR^b$, where $R^a$ and $R^b$ each independently represent H, $C_{1-6}$alkyl, phenyl or trifluoromethyl;

$R^2$ represents phenyl optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$CO_2R^a$ or —$CONR^aR^b$, where $R^a$ and $R^b$ are as previously defined; heteroaryl selected from indazolyl, thienyl, furyl, pyridyl, thiazolyl, tetrazolyl and quinolyl; benzhydryl; or benzyl; wherein each heteroaryl and each phenyl moiety of benzyl and benzhydryl may be substituted by $C_{1-6}$alkyl, $C_{1-6}$alkoxy, halo or trifluoromethyl;

$R^3$ represents H, $COR^9$, $CO_2R^{10}$, $COCONR^{10}R^{11}$, $COCO_2R^{10}$, $SO_2R^{15}$ $CONR^{10}SO_2R^{15}$, $C_{1-6}$alkyl optionally substituted by a group selected from ($CO_2R^{10}$, $CONR^{10}R^{11}$, hydroxy, cyano, $COR^9$, $NR^{10}R^{11}$, C(NOH)$NR^{10}R^{11}$, CONHphenyl($C_{1-4}$alkyl), $COCO_2R^{10}$, $COCONR^{10}R^{11}$, $SO_2R^{15}$, $CONR^{10}SO_2R^{15}$ and phenyl optionally substituted by one or more substituents selected from $C_{1-6}$alkyl, $C_{1-6}$alkoxy, halo and trifluoromethyl), Y—$R^8$ or CO—Z—$(CH_2)_q$—$R^{12}$;

$R^4$ is $C_{1-6}$alkyl substituted by a hydroxy group, or $(CH_2)_p$$NR^{10}R^{11}$, $CO_2R^{16}$, $CONR^{10}R^{11}$, $(CH_2)_pCO_2R^{16}$, $(CH_2)_pCONR^{10}R^{11}$, $(CH_2)_pNR^{10}COR^{16}$, $(CH_2)_p$$NHSO_2R^{12}$, $(CH_2)_pOR^{16}$, $(CH_2)_pOC(O)R^{10}$ or $(CH_2)_p$$O(CH_2)_rCOR^{17}$;

$R^5$, $R^6$ and $R^7$ each independently represent H or $C_{1-6}$alkyl;

$R^8$ represents an optionally substituted aromatic heterocycle;

$R^9$ represents H, $C_{1-6}$alkyl or phenyl;

$R^{10}$ and $R^{11}$ each independently represent H or $C_{1-6}$alkyl;

$R^{12}$ represents $NR^{13}R^{14}$ or an optionally substituted aromatic or non-aromatic azacyclic or azabicyclic group;

$R^{13}$ and $R^{14}$ each independently represent H, $C_{1-6}$alkyl, phenyl optionally substituted by one or more of $C_{1-6}$alkyl, $C_{1-6}$alkoxy, halo or trifluoromethyl or phenyl$C_{1-4}$alkyl optionally substituted in the phenyl ring by one or more of $C_{1-6}$alkyl, $C_{1-6}$alkoxy, halo or trifluoromethyl;

$R^{15}$ represents $C_{1-6}$alkyl, trifluoromethyl or phenyl optionally substituted by one or more substituents selected from $C_{1-6}$alkyl, $C_{1-6}$alkoxy, halo and trifluoromethyl;

$R^{16}$ represents $C_{1-6}$alkyl;

$R^{17}$ represents $C_{1-6}$alkoxy, amino, $C_{1-4}$alkylamino or di($C_{1-4}$alkyl)amino;

Y represents a hydrocarbon chain of 1, 2, 3 or 4 carbon atoms which may optionally be substituted by oxo;

Z represents $CH_2$, O, S or $NR^{10}$;

p represents 1 to 4;

q represents zero, 1, 2, 3, 4, 5 or 6;

r represents 1 to 4;

X represents O or $NR^{19}$ where $R^{19}$ represents hydrogen or $C_{1-6}$ alkyl, or a pharmaceutically acceptable salt thereof.

4. A compound as claimed in claim 1 of formula (Ia):

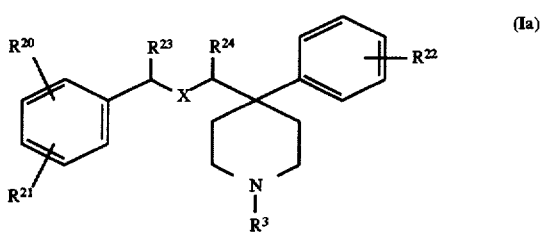

(Ia)

wherein $R^3$ and X are as defined in claim 1;

$R^{20}$ and $R^{21}$ independently represent H, $C_{1-6}$alkyl, $C_{2-6}$alkenyl, $C_{2-6}$alkynyl, $C_{3-6}$cycloalkyl, $C_{3-6}$cycloalkyl$C_{1-4}$alkyl, halo, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $COR^a$, $CO_2R^a$ or $CONR^aR^b$, where $R^a$ and $R^b$ are as previously defined in claim 1;

$R^{22}$ represents H or halo;

$R^{23}$ is $C_{1-6}$alkyl substituted by a hydroxy group; and $R^{24}$ is H or methyl; or a pharmaceutically acceptable salt thereof.

5. A compound selected from:

4-phenyl-4-((1-(3,5-bis(trifluoromethyl)phenyl)-2-hydroxyethoxy)methyl) piperidine;

4-phenyl-4-((1-(3,5-bis(trifluoromethyl)phenyl)-2-methoxyethoxy)methyl) piperidine;

4-phenyl-4-((1-(3,5-bis(trifluoromethyl )phenyl)-2-ethoxyethoxy)methyl) piperidine;

4-phenyl-4-((1-(3,5-bis(trifluoromethyl)phenyl)-2-cyclopropylmethoxyethoxy) methyl)piperidine;

4-phenyl-4-((1-(3,5-bis(trifluoromethyl)phenyl)-2-methoxycarbonyl-methoxyethoxy)methyl)piperidine;

4-phenyl-4-((1-(3,5-bis(trifluoromethyl)phenyl)-2-acetoxyethoxy)methyl) piperidine;

5[(4-phenyl-4-((1-(3,5-bis(trifluoromethyl)phenyl)-2-hydroxyethoxy)methyl) piperidin-1-yl)methyl]-2,4-dihydro-[1,2,4]-triazol-3-one;

4-phenyl-4-((1-(3,5-bis(trifluoromethyl)phenyl)-2-hydroxyethoxy)methyl)-1-(2-(1-pyrrolidinyl) acetamido)piperidine;

methyl 2-(4-phenylpiperidin-4-yl)methoxy-2-(3,5-bis (trifluoromethyl)phenyl) acetate;

isopropyl 2-(4-phenylpiperidin-4-yl)methoxy-2-(3,5-bis (trifluoromethyl)phenyl) acetate;

4-phenyl-4-[(1-(3,5-bis(trifluoromethyl )phenyl )-2-hydroxy-2-methylpropyloxy) methyl]piperidine;

2-(4-phenylpiperidin-4-yl)methoxy-2-(3,5-bis (trifluoromethyl)phenyl) acetamide;

4-phenyl-4-[(1-(3,5-bis(trifluoromethyl)phenyl)-2-aminoethoxy)methyl] piperidine;

4-phenyl-4-[(1-(3-fluoro-5-trifluoromethylphenyl)-2-hydroxyethoxy)methyl] piperidine;

5-[4-phenyl-4-[(1-(3-fluoro-5-trifluoromethylphenyl)-2-hydroxyethoxy)methyl] piperidin-1-ylmethyl]-2,4-dihydro-[1,2,4]-triazol-3-one;

4-phenyl-4-[(1-(3-fluoro-5-trifluoromethylphenyl)-2-hydroxyethoxy)methyl]-1-(2-(pyrrolidinyl)acetamido) piperidine;

4-phenyl-4-[(1-(3,5-bis(trifluoromethyl)phenyl)-2-(3-methylureido)ethoxy) methyl]piperidine;

4-phenyl-4-[(1-(3,5-bis(trifluoromethyl)phenyl)-2-acetamido)methyl]piperidine;

4-phenyl-4-[(1-(3,5-bis(trifluoromethyl)phenyl)-2-methansulphonamido) methyl]piperidine;

4-phenyl-4-[(1-(3,5-bis(trifluoromethyl)phenyl)-2-(carbomethoxymethoxy) ethoxy)methyl]piperidine;

4-(4-fluorophenyl)4-[(1-(3,5-bis(trifluoromethyl)phenyl)-2-hydroxyethoxy)methyl]-1-(2-(1-pyrrolidinyl) acetamido)piperidine;

(+)4-(4-fluorophenyl)-4-[(1-(3, 5-bis(trifluoromethyl) phenyl)-2-hydroxyethoxy)methyl]-1-(2-(1-pyrrolidinyl)acetamido)piperidine;

4-phenyl-4-[(1-(3,5-bis(trifluoromethyl)phenyl)-1-hydroxymethyl-2-hydroxyethoxy)methyl]piperidine;

5-[(4-phenyl-4-((1-(3,5-bis(trifluoromethyl)phenyl)-1-hydroxymethyl-2-hydroxyethoxy)methyl)piperidin-1-ylmethyl]-2,4-dihydro-[1,2,4]-triazol-3-one;

4-phenyl-4-[(1-(3,5-bis(trifluoromethyl)phenyl) cyclopropyloxy)methyl] piperidine;

4-phenyl4-[(1-(3,5-bis(trifluoromethyl)phenyl) cyclopropyloxy)methyl]-1-(2-(1-pyrrolidinyl) acetamido)piperidine;

4-phenyl-4-[(1-(3,5-bis(trifluoromethyl)phenyl)-1-methyl-2-hydroxyethoxy) methyl]piperidine;

5-[4-phenyl-4-[(1-(3,5-bis(trifluoromethyl)phenyl)-1-methyl-2-hydroxyethoxy) methyl]piperidin-1-yl) methyl]-2,4-dihydro-[1,2,4]-triazol-3-one;

or a pharmaceutically acceptable acid addition salt thereof.

6. A pharmaceutical composition comprising a compound as claimed in claim 1 in association with a pharmaceutically acceptable carrier or excipient.

7. A method for the treatment or prevention of physiological disorders associated with an excess of tachykinins, which method comprises administration to a patient in need thereof of a tachykinin reducing amount of a compound according to claim 1, or a pharmaceutically acceptable salt thereof.

8. A method according to claim 7 for the treatment or prevention of pain or inflammation.

9. A method according to claim 7 for the treatment or prevention of migraine.

10. A method according to claim 7 for the treatment or prevention of emesis.

11. A process for the preparation of a compound of formula (I) which comprises:

(A) reacting a compound of the formula (II) with a compound of the formula (III)

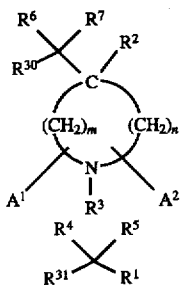

(III)

wherein $A^1$, $A^2$, $R^1$, $R^2$, $R^3$) $R^4$, $R^5$, $R^6$, $R^7$, m and n are as defined in claim 1, or a protected derivative thereof; and one of $R^{30}$ and $R^{31}$ represents a leaving group and the other represents a OH or $NR^{19}$ group where $R^{19}$ is as defined in claim 1; in the presence of base followed by deprotection if required; or (B) by interconversion of a compound of formula (I) into another compound of formula (I);

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resultant compound of formula (I) or a salt thereof into a pharmaceutically acceptable salt thereof.

* * * * *